(12) United States Patent
Sonne et al.

(10) Patent No.: US 12,297,251 B1
(45) Date of Patent: May 13, 2025

(54) INJECTION PEN FOR SUBCUTANEOUS ADMINISTRATION OF A PEPTIDE

(71) Applicant: Zealand Pharma A/S, Søborg (DK)

(72) Inventors: Kim Sonne, Søborg (DK); Ulrik Mouritzen, Søborg (DK); Peter Glerup, Søborg (DK)

(73) Assignee: Zealand Pharma A/S, Søborg (DK)

( * ) Notice: Subject to any disclaimer, the term of this patent is extended or adjusted under 35 U.S.C. 154(b) by 0 days.

(21) Appl. No.: 18/496,636

(22) Filed: Oct. 27, 2023

Related U.S. Application Data

(63) Continuation of application No. 16/511,766, filed on Jul. 15, 2019, now abandoned, which is a continuation of application No. PCT/EP2018/065951, filed on Jun. 15, 2018.

(30) Foreign Application Priority Data

| Jun. 16, 2017 | (GB) | .................................... 1709643 |
| Sep. 5, 2017 | (GB) | .................................... 1714203 |
| Jan. 19, 2018 | (GB) | .................................... 1800873 |

(51) Int. Cl.
*C07K 14/605* (2006.01)
*A61K 9/00* (2006.01)

(52) U.S. Cl.
CPC .......... *C07K 14/605* (2013.01); *A61K 9/0024* (2013.01)

(58) Field of Classification Search
None
See application file for complete search history.

(56) References Cited

U.S. PATENT DOCUMENTS

| | | |
|---|---|---|
| 5,432,156 A | 7/1995 | Matsuno et al. |
| 5,789,379 A | 8/1998 | Drucker et al. |
| 5,834,428 A | 11/1998 | Drucker |
| 5,912,229 A | 6/1999 | Thim et al. |
| 5,952,301 A | 9/1999 | Drucker |
| 5,990,077 A | 11/1999 | Drucker |
| 5,994,500 A | 11/1999 | Drucker et al. |
| 6,051,557 A | 4/2000 | Drucker |
| 6,184,201 B1 | 2/2001 | Drucker et al. |
| 6,184,208 B1 | 2/2001 | Deigin et al. |
| 6,297,214 B1 | 10/2001 | Drucker |
| 6,489,295 B1 | 12/2002 | Drucker et al. |
| 6,586,399 B1 | 7/2003 | Drucker |
| 6,677,136 B2 | 1/2004 | Marshall et al. |
| 6,770,620 B2 | 8/2004 | Henriksen |
| 7,049,284 B2 | 5/2006 | Drucker |
| 7,176,182 B2 | 2/2007 | Drucker |
| 7,186,683 B2 | 3/2007 | Henriksen et al. |
| 7,371,721 B2 | 5/2008 | Henriksen et al. |
| 7,411,039 B2 | 8/2008 | Thim et al. |
| 7,563,770 B2 | 7/2009 | Larsen et al. |
| 7,737,251 B2 | 6/2010 | Bridon et al. |
| 7,745,403 B2 | 6/2010 | Larsen et al. |
| 8,163,696 B2 | 4/2012 | Larsen et al. |
| 8,263,552 B2 | 9/2012 | Larsen et al. |
| 8,642,727 B2 | 2/2014 | Larsen et al. |
| 9,125,882 B2 | 9/2015 | Larsen et al. |
| 9,453,064 B2 | 9/2016 | Just et al. |
| 9,580,487 B2 | 2/2017 | Larsen et al. |
| 9,969,787 B2 | 5/2018 | Just et al. |
| 10,092,648 B2 | 10/2018 | Larsen et al. |
| 10,442,847 B2 | 10/2019 | Riber et al. |
| 2001/0021767 A1 | 9/2001 | Drucker et al. |
| 2002/0025933 A1 | 2/2002 | Knudsen et al. |
| 2003/0040478 A1 | 2/2003 | Drucker et al. |
| 2003/0109449 A1 | 6/2003 | Drucker et al. |
| 2003/0158101 A1 | 8/2003 | Drucker |
| 2003/0162703 A1 | 8/2003 | Drucker et al. |
| 2003/0207809 A1 | 11/2003 | Drucker |
| 2004/0052862 A1 | 3/2004 | Henriksen et al. |
| 2004/0122210 A1 | 6/2004 | Thim et al. |
| 2004/0127418 A1 | 7/2004 | Knudsen et al. |
| 2004/0198642 A1 | 10/2004 | Drucker et al. |
| 2004/0248782 A1 | 12/2004 | Bridon et al. |
| 2005/0256044 A1 | 11/2005 | Boyle et al. |
| 2005/0282749 A1 | 12/2005 | Henriksen et al. |
| 2006/0105954 A1 | 5/2006 | Drucker |
| 2006/0135424 A1 | 6/2006 | Sanguinetti et al. |
| 2007/0117752 A1* | 5/2007 | Larsen ................. C07K 14/605 514/19.3 |
| 2007/0231308 A1 | 10/2007 | Larsen et al. |
| 2009/0028832 A1 | 1/2009 | Chung et al. |
| 2009/0082309 A1 | 3/2009 | Bachovchin et al. |
| 2009/0105341 A1 | 4/2009 | Stanton |
| 2011/0098222 A1 | 4/2011 | Larsen et al. |
| 2011/0152186 A1 | 6/2011 | Larsen et al. |

(Continued)

FOREIGN PATENT DOCUMENTS

| CN | 101171262 A | 4/2008 |
| CN | 101331224 A | 12/2008 |

(Continued)

OTHER PUBLICATIONS

Lucidi et al., "Metabolism of insulin glargine after repeated daily subcutaneous injections in subjects with type 2 diabetes," Diabetes Care 35(12):2647-9 (Dec. 2012).

Agin et al., "Glargine blood biotransformation: in vitro appraisal with human insulin immunoassay," Diabetes Metab. 33(3):205-12 (Jun. 2007).

Manea et al., "Mass spectrometric identification of the trypsin cleavage pathway in lysyl-proline containing oligotuftsin peptides," J Pept Sci. 13(4):227-36 (Apr. 2007).

Agersnap et al., "Pharmacokinetics of Glepaglutide, A Long-Acting Glucagon-Like Peptide-2 Analogue: A Study in Healthy Subjects," Clin Drug Investig. 42(12):1093-100 (Dec. 2022).

Declaration of Mark Berner-Hansen in the Matter of Examination of European Patent No. 3 881 861 A, dated Jun. 7, 2023 (17 pages).

Korner et al., "GLP-2 receptors in human disease: high expression in gastrointestinal stromal tumors and Crohn's disease," Mol Cell Endocrinol. 364(1-2):46-53 (Nov. 2012).

(Continued)

*Primary Examiner* — Maury A Audet
(74) *Attorney, Agent, or Firm* — Clark & Elbing LLP

(57) ABSTRACT

The invention features injection pens for the subcutaneous injection of a peptide and methods of using same.

9 Claims, No Drawings

Specification includes a Sequence Listing.

(56) References Cited

U.S. PATENT DOCUMENTS

| | | |
|---|---|---|
| 2011/0288003 A1 | 11/2011 | DiMarchi et al. |
| 2012/0004392 A1 | 1/2012 | Larsen et al. |
| 2012/0178676 A1 | 7/2012 | Barrack et al. |
| 2012/0289466 A1 | 11/2012 | Larsen et al. |
| 2013/0123462 A1 | 5/2013 | Dimarchi et al. |
| 2013/0281374 A1 | 10/2013 | Levy et al. |
| 2014/0154214 A1 | 6/2014 | Larsen et al. |
| 2015/0125431 A1 | 5/2015 | Just et al. |
| 2016/0355563 A1 | 12/2016 | Just et al. |
| 2017/0137487 A1 | 5/2017 | Larsen et al. |
| 2020/0000883 A1 | 1/2020 | Sonne et al. |
| 2020/0254065 A1 | 8/2020 | Hershkovitz et al. |
| 2022/0265551 A1 | 8/2022 | Giehm et al. |

FOREIGN PATENT DOCUMENTS

| | | |
|---|---|---|
| CN | 102212127 A | 10/2011 |
| EP | 1231218 B1 | 8/2002 |
| EP | 1231219 A1 | 8/2002 |
| EP | 0891378 B1 | 11/2002 |
| EP | 0906338 B1 | 11/2002 |
| EP | 0981362 B1 | 11/2003 |
| EP | 0830377 B1 | 10/2009 |
| EP | 1414486 B1 | 5/2010 |
| EP | 3628683 A1 | 4/2020 |
| WO | WO-96/32414 A1 | 10/1996 |
| WO | WO-97/31943 A1 | 9/1997 |
| WO | WO-97/39031 A1 | 10/1997 |
| WO | WO-98/03547 A1 | 1/1998 |
| WO | WO-98/11125 A1 | 3/1998 |
| WO | WO-98/52600 A1 | 11/1998 |
| WO | WO-99/46283 A1 | 9/1999 |
| WO | WO-99/58144 A1 | 11/1999 |
| WO | WO-01/04156 A1 | 1/2001 |
| WO | WO-01/41779 A2 | 6/2001 |
| WO | WO-01/49314 A2 | 7/2001 |
| WO | WO-02/24214 A2 | 3/2002 |
| WO | WO-02/066511 A2 | 8/2002 |
| WO | WO-02/098348 A2 | 12/2002 |
| WO | WO-2004/035624 A2 | 4/2004 |
| WO | WO-2004/039392 A2 | 5/2004 |
| WO | WO-2005/027978 A2 | 3/2005 |
| WO | WO-2005/049061 A2 | 6/2005 |
| WO | WO-2005/082404 A2 | 9/2005 |
| WO | WO-2006/050244 A2 | 5/2006 |
| WO | WO-2006/117565 A2 | 11/2006 |
| WO | WO-2007/022123 A2 | 2/2007 |
| WO | WO-2008/056155 A1 | 5/2008 |
| WO | WO-2008/084237 A2 | 7/2008 |
| WO | WO-2008082656 A1 | 7/2008 |
| WO | WO-2008/101017 A2 | 8/2008 |
| WO | WO-2009/155258 A2 | 12/2009 |
| WO | WO-2010/070251 A1 | 6/2010 |
| WO | WO-2010/099746 A1 | 9/2010 |
| WO | WO-2011/075393 A2 | 6/2011 |
| WO | WO-2011/117417 A1 | 9/2011 |
| WO | WO-2011/160630 A2 | 12/2011 |
| WO | WO-2012/158965 A2 | 11/2012 |
| WO | WO-2013/040093 A2 | 3/2013 |
| WO | WO-2013/164484 A1 | 11/2013 |
| WO | WO-2014/016300 A1 | 1/2014 |
| WO | WO-2014/124151 A1 | 8/2014 |
| WO | WO-2016/038455 A1 | 3/2016 |
| WO | WO-2016/065181 A1 | 4/2016 |
| WO | WO-2016/102683 A1 | 6/2016 |
| WO | WO-2016/133863 A1 | 8/2016 |
| WO | WO-2017/053822 A1 | 3/2017 |
| WO | WO-2018/094404 A1 | 5/2018 |
| WO | WO-2018/104561 A1 | 6/2018 |
| WO | WO-2018/142363 A1 | 8/2018 |
| WO | WO-2018/229252 A1 | 12/2018 |
| WO | WO-2019008033 A1 | 1/2019 |
| WO | WO-2019/110838 A1 | 6/2019 |
| WO | WO-2020/020904 A1 | 1/2020 |

OTHER PUBLICATIONS

Invitation to Remedy Deficiencies Pursuant to Rule 30(3) EPC / Rule 163(3) EPC for European Application No. 21150552.4, dated Mar. 2, 2021 (2 pages).
Communication pursuant to Rule 19(1) EPC for European Patent Application No. 21150552.4, dated Apr. 6, 2021 (1 page).
Letter accompanying subsequently filed items for European Patent Application No. 21150552.4, dated Apr. 28, 2021 (2 pages).
Reply to Invitation to Remedy Deficiencies Pursuant to Rule 30(3) EPC / Rule 163(3) EPC for European Patent Application No. 21150552.4, dated Apr. 27, 2021 (1 page).
European Search Report for European Patent Application No. 21150552.4, mailed Aug. 10, 2021 (7 pages).
Communication enclosing the Extended European Search Report for European Patent Application No. 21150552.4, dated Aug. 10, 2021 (1 page).
European Search Opinion for European Patent Application No. 21150552.4, dated Aug. 10, 2021 (5 pages).
Information on Search Strategy for European Patent Application No. 21150552.4, dated Aug. 10, 2021 (1 page).
Letter accompanying subsequently filed items for European Patent Application No. 21150552.4, dated May 4, 2022 (2 pages).
Response to Communication for European Patent Application No. 21150552.4 including Amended Claims and Amended Description, dated May 4, 2022 (31 pages).
Communication Pursuant to Article 94(3) EPC for European Patent Application No. 21150552.4, dated Oct. 4, 2022 (5 pages).
Letter accompanying subsequently filed items for European Application No. European Patent Application No. 21150552.4, dated Jun. 16, 2023 (2 pages).
Response to Communication for European Patent Application No. 21150552.4 including Amended Claims and Amended Description, dated Jun. 16, 2023 (21 pages).
Communication under Rule 71(3) EPC for European Patent Application No. 21150552.4, dated Oct. 31, 2024 (101 pages).
Letter accompanying subsequently filed items for European Patent Application No. 21150552.4, dated Nov. 15, 2023 (1 page).
Response to Communication for European Patent Application No. 21150552.4, dated Nov. 15, 2023 (6 pages).
Communication under Rule 71(3) EPC for European Patent Application No. 21150552.4, dated Dec. 1, 2023 (101 pages).
Letter accompanying subsequently filed items for European Patent Application No. 21150552.4, dated Feb. 13, 2024 (1 page).
Response to Communication for European Patent Application No. 21150552.4, dated Feb. 13, 2024 (9 pages).
Communication under Rule 71(3) EPC for European Patent Application No. 21150552.4, dated Mar. 1, 2024 (101 pages).
Letter accompanying subsequently filed items for European Patent Application No. 21150552.4, dated Jun. 20, 2024 (2 pages).
Decision to Grant a European Patent Pursuant to Article 97(1) EPC for European Patent Application No. 21150552.4, dated Jul. 4, 2024 (3 pages).
Transmission of the Certificate for a European Patent Pursuant to Rule 74 EPC for European Patent Application No. 21150552.4, dated Aug. 13, 2024 (1 page).
U.S. Appl. No. 18/496,597, Sonne et al.
"Zollinger-Ellison Syndrome", The National Institute of Diabetes and Digestive and Kidney Diseases, <https://www.niddk.nih.gov/health-information/digestive-diseases/zollinger-ellison-syndrome>, accessed Oct. 16, 2017 (10 pages).
A Phase 2 Trial Testing ZP1848 in Patients with SBS (glepaglutide). ClinicalTrials.gov Identifier: NCT02690025, dated Feb. 18, 2016 (10 pages).
A Phase 2 Trial Testing ZP1848 in Patients with SBS (glepaglutide). ClinicalTrials.gov Identifier: NCT02690025, dated Jun. 20, 2017 (10 pages).
Agersnap et al., "Glepaglutide Pharmacokinetic Profile After Single Subcutaneous Injection in Human Subjects With Varying Degrees of Renal Function," Clin Nutr ESPEN. 47: 666-667 (Dec. 2021).
Akers et al., Chapter 2: Formulation Development of Protein Dosage Forms. *Development and Manufacture of Protein Pharma-*

(56) References Cited

OTHER PUBLICATIONS

*ceuticals.* ed. Steven L. Nail and Michael J. Akers. New York: Kluwer Academic/Plenum Publishers, 2002, pp. 47-127 (83 pages).
Alison et al., "The role of growth factors in gastrointestinal cell proliferation," Cell Biol Int. 18(1):1-10 (1994).
Alters et al., "GLP2-2G-XTEN: a pharmaceutical protein with improved serum half-life and efficacy in a rat Crohn's disease model," PLoS One. 7(11):e50630 (2012) (11 pages).
Altschul et al., "Local alignment statistics," Methods Enzymol. 266:460-480 (1996).
Baldassano et al., "GLP-2: What do we know? What are we going to discover?," Regul Pept. 194-195:6-10 (2014).
Baldwin et al., "Gut hormones, growth and malignancy," Bailliére's Clin Endocrinol Metab. 8(1):185-214 (1994).
Bamba et al., "Enteroglucagon. A putative humoral factor including pancreatic hyperplasia after proximal small bowel resection," Dig Dis Sci. 39(7):1532-36 (1994).
Barragán et al., "Changes in arterial blood pressure and heart rate induced by glucagon-like peptide-1-(7-36) amide in rats," Am J Physiol. 266(3 Pt1):E459-66 (1994).
Benjamin et al., "Glucagon-like peptide-2 enhances intestinal epithelial barrier function of both transcellular and paracellular pathways in the mouse," Gut. 47(1):112-9 (2000).
Bloom, "Gut hormones in adaptation," Gut. 28(Suppl):31-5 (1987).
Booth et al., "Teduglutide ([Gly2]GLP-2) protects small intestinal stem cells from radiation damage," Cell Prolif. 37(6):385-400 (2004).
Boushey et al., "Glucagon-like peptide (GLP)-2 reduces chemotherapy-associated mortality and enhances cell survival in cells expressing a transfected GLP-2 receptor," Cancer Res. 61(2):687-93 (2001).
Boushey et al., "Glucagon-like peptide 2 decreases mortality and reduces the severity of indomethacin-induced murine enteritis," Am J Physiol. 227(5 Pt 1):E937-47 (1999).
Bowie et al., "Deciphering the message in protein sequences: tolerance to amino acid substitutions," Science. 247(4948):1306-10 (1990).
Brubaker et al., "Alterations in proglucagon processing and inhibition of proglucagon gene expression in transgenic mice which contain a chimeric proglucagon-SV40 T antigen gene," J Biol Chem. 267(29):20728-33 (1992).
Bulik, "The challenges of treating anorexia nervosa," Lancet 383(9912):105-6 (Jan. 11, 2014).
Canada, "Teduglutide: a novel recombinant analog of human glucagon-like peptide-2 for short bowel syndrome," Formulary. 47(9):314-8 (2012).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Cheeseman, "Upregulation of SGLT-1 transport activity in rat jejunum induced by GLP-2 infusion in vivo," Am J Physiol. 273(6 Pt 2):R1965-71 (1997).
Code, "The digestive system," Annu Rev Physiol. 15:107-38 (1953).
Creson et al., "Powdered duodenal extract in the treatment of peptic ulcer," Am J Gastroenterol. 33:359-65 (1960).
DaCambra et al., "Structural determinants for activity of glucagon-like peptide-2," Biochemistry. 39(30):8888-94 (2000).
Dalvi et al., "Glucagon-like peptide-2 directly regulates hypothalamic neurons expressing neuropeptides linked to appetite control in vivo and in vitro," Endocrinology 153(5):2385-97 (May 2012).
Drucker et al., "Biologic properties and therapeutic potential of glucagon-like peptide-2," JPEN J Patenter Enteral Nutr. 23(5):S98-100 (1999).
Drucker et al., "Human [Gly2]GLP-2 reduces the severity of colonic injury in a murine model of experimental colitis," Am J Physiol. 276(1 Pt 1):G79-91 (1999).
Drucker et al., "Induction of intestinal epithelial proliferation by glucagon-like peptide 2," Proc Nat Acad Sci U.S.A. 93(15):7911-6 (1996).

Drucker et al., "Physiology and pharmacology of the enteroendocrine hormone glucagon-like peptide-2," Annu Rev Physiol. 76:561-83 (2014).
Drucker et al., "Regulation of the biological activity of glucagon-like peptide 2 in vivo by dipeptidyl peptidase IV," Nat Biotechnol. 15(7):673-7 (1997).
Drucker, "Glucagon-like peptide 2," J Clin Endocrinol Metab. 86(4):1759-64 (2001).
Drucker, "Minireview: The glucagon-like peptides," Endocrinology. 142(2):521-7 (2001).
Estall et al., "Dual Regulation of Cell Proliferation and Survival via Activation of Glucagon-Like Peptide-2 Receptor Signaling," J Nutr. 133(11):3708-11 (2003).
Fallacara et al., "Hyaluronic Acid in the Third Millennium," Polymers (Basel) 10(7):701 (Jun. 25, 2018) (36 pages).
Feinberg et al., "Period and amplitude analysis of 0.5-3 c/sec activity in NREM sleep of young adults," Electroencephalogr Clin Neurophysiol. 44(2):202-13 (1978).
Ferrone et al., "Teduglutide for the treatment of short bowel syndrome," Ann Pharmacother. 40(6):1105-9 (2006).
Gadermann et al., "[Treatment of gastroduodenal ulcerations & inflammations with the tissue extract robadin]," Med Klin (Munich). 54(16):774-8 (1959).
Gibson et al., "Irinotecan causes severe small intestinal damage, as well as colonic damage, in the rat with implanted breast cancer," J Gastroenterol Hepatol. 18(9):1095-100 (2003).
Gibson et al., "Relative roles of spatial and intensive cues in the discrimination of spatial tactile stimuli," Percept Pyschophys. 64(7):1095-107 (2002).
Glass et al., "Studies on robuden, extract from stomach and duodenum: its effects upon gastric secretion and clinical course of peptic ulcer," Am J Dig Dis. 4(12):988-1013 (1959).
Gregor et al., "The role of gut-glucagon-like immunoreactants in the control of gastrointestinal epithelial cell renewal," Digestion. 46(Suppl 2):59-65 (1990).
Grey et al., "A growth-stimulating activity derived from the proximal small intestine is associated with an adaptive response," Can J Physiol Pharmacol. 68(5):646-9 (1990).
Grey et al., "Detection of growth-stimulating activity in the proximal small intestine during weaning in the suckling rat," Biol Neonate. 59(1):37-45 (1991).
Grey et al., "Evidence for a growth-stimulating fraction in the rat proximal intestine after small bowel resection," Gastroenterology. 89(6):1305-12 (1985).
Guan et al., "GLP-2-mediated up-regulation of intestinal blood flow and glucose uptake is nitric oxide-dependent in TPN-fed piglets," Gastroenterology. 125(1):136-47 (2003).
Hargrove et al., "Pharmacological Characterization of Apraglutide, a Novel Long-Acting Peptidic Glucagon-Like Peptide-2 Agonist, for the Treatment of Short Bowel Syndrome," J Pharmacol Exp Ther. 373(2):193-203 (May 2020).
International Preliminary Report on Patentability from PCT/GB2006/001633, mailed Nov. 6, 2007 (10 pages).
International Preliminary Report on Patentability from PCT/GB2007/004273, mailed May 12, 2009 (9 pages).
International Search Report and Written Opinion for International Application No. PCT/EP2013/059320, mailed on Aug. 8, 2013 (11 pages).
International Search Report and Written Opinion for PCT/EP2018/065951, mailed Nov. 6, 2018 (18 pages).
International Search Report and Written Opinion for PCT/EP2021/085846, mailed Apr. 7, 2022 (11 pages).
International Search Report from PCT/GB2006/001633, mailed Oct. 24, 2006 (6 pages).
International Search Report from PCT/GB2007/004273, mailed Apr. 14, 2008 (4 pages).
Irwin et al., "Trout and chicken proglucagon: alternative splicing generates mRNA transcripts encoding glucagon-like peptide 2," Mol Endocrinol. 9(3):267-77 (1995).
Ivory et al., "Interleukin-10-independent anti-inflammatory actions of glucagon-like peptide 2," Am J Physiol Gastrointest Liver Physiol. 295(6): G1202-10 (2008).

(56) References Cited

OTHER PUBLICATIONS

Jenkins et al., "Mechanisms of small intestinal adaptation," Dig Dis. 12(1):15-27 (1994).
Jeppesen et al., "Quality of life in patients with short bowel syndrome treated with the new glucagon-like peptide-2 analogue teduglutide-analyses from a randomised, placebo-controlled study," Clin Nutr. 32(5):713-21 (2013).
Jeppesen et al., "Randomised placebo-controlled trial of teduglutide in reducing parenteral nutrition and/or intravenous fluid requirements in patients with short bowel syndrome," Gut. 60(7):902-14 (2011).
Jeppesen et al., "Teduglutide (ALX-0600), a dipeptidyl peptidase IV resistant glucagon-like peptide 2 analogue, improves intestinal function in short bowel syndrome patients," Gut. 54(9):1224-31 (2005).
Jeppesen et al., "Teduglutide reduces need for parenteral support among patients with short bowel syndrome with intestinal failure," Gastroenterology. 143(6):1473-81 (including supplemental content) (2012) (12 pages).
Jeppesen, "Teduglutide, a novel glucagon-like peptide 2 analog, in the treatment of patients with short bowel syndrome," Ther Adv Gastroenterol. 5(3):159-71 (2012).
Jeppesen, "The use of hormonal growth factors in the treatment of patients with short-bowel syndrome," Drugs. 66(5):581-9 (2006).
Kaye et al., "Treatment of Patients With Anorexia Nervosa in the US-A Crisis in Care," JAMA Psychiatry 78(6):591-2 (Jun. 1, 2021).
Keefe et al., "Chemotherapy for cancer causes apoptosis that precedes hypoplasia in crypts of the small intestine in humans," Gut. 47(5):632-7 (2000).
Kieffer et al., "The glucagon-like peptides," Endocr Rev. 20(6):876-913 (1999).
Kochar et al., "Safety and Efficacy of Teduglutide (Gattex) in Patients With Crohn's Disease and Need for Parenteral Support Due to Short Bowel Syndrome associated Intestinal Failure," available in PMC Jul. 1, 2018, published in final edited form as: J Clin Gastroenterol. 51(6):508-11 (Jul. 2017) (10 pages).
Kyte et al., "A simple method for displaying the hydropathic character of a protein," J Mol Biol. 157(1):105-32 (1982).
Larsen et al., "Incomplete Fmoc deprotection in solid-phase synthesis of peptides," Int J Pept Protein Res. 43(1):1-9 (1994).
Lee et al., "Enteroendocrine-derived glucagon-like peptide-2 controls intestinal amino acid transport," Mol Metab. 6(3):245-255 (Jan. 2017).
Lentze, "Intestinal adaptation in short-bowel syndrome," Eur J Pediatr. 148(4):294-9 (1989).
Lopez et al., "Mammalian pancreatic preproglucagon contains three glucagon-related peptides," Proc Natl Acad Sci U.S.A. 80(18):5485-9 (1983).
Meier et al., "Glucagon-like peptide 2 stimulates glucagon secretion, enhances lipid absorption, and inhibits gastric acid secretion in humans," Gastroenterology. 130(1):44-54 (2006).
Mentlein et al., "Dipeptidyl-peptidase IV hydrolyses gastric inhibitory polypeptide, glucagon-like peptide-1(7-36)amide, peptide histidine methionine and is responsible for their degradation in human serum," Eur J Biochem. 214(3):829-35 (1993).
Miazza et al., "Hyperenteroglucagonaemia and small intestinal mucosal growth after colonic perfusion of glucose in rats," Gut. 26(5):518-24 (1985).
Monteleone et al. "Intestinal Permeability is Decreased in Anorexia Nervosa," Mol Psychiatry. 9(1):76-80 (2004) (5 pages).
Moon et al., "Tyr1 and Ile7 of glucose-dependent insulinotropic polypeptide (GIP) confer differential ligand selectivity toward GIP and glucagon-like peptide-1 receptors," Mol Cells. 30(2):149-54 (2010).
Moore et al., "GLP-2 receptor agonism ameliorates inflammation and gastrointestinal stasis in murine postoperative ileus," J Pharmacol Exp Ther. 333(2):574-83 (2010).
Myojo et al., "Trophic effects of glicentin on rat small-intestinal mucosa in vivo and in vitro," J Gastroenterol. 32(3):300-5 (1997) (English abstract).

Naimi et al., "A dose-equivalent comparison of the effects of continuous subcutaneous glucagon-like peptide 2 (GLP-2) infusions versus meal related GLP-2 injections in the treatment of short bowel syndrome (SBS) patients," Regul Pept. 184:47-53 (Jun. 10, 2013).
Naimi et al., "Glepaglutide, a novel long-acting glucagon-like peptide-2 analogue, for patients with short bowel syndrome: a randomised phase 2 trial," Lancet Gastroenterol Hepatol. 4(5):354-363 (Mar. 2019).
Neumann, "Experiences with medications: A review of 12 years of peptic ulcer treatment with Robuden," Schweiz Med Wochenschr. 87(32):1049-1051 (1957).
Notice of Opposition for European Patent No. EP1877435, mailed on Nov. 22, 2011 (29 pages).
Notkin et al., "Gastroduodenal tissue extracts in the treatment of peptic ulcer with special reference to the effectiveness of robuden," Am J Dig Dis. 21(9):251-61 (1954).
Oben et al., "Effect of the entero-pancreatic hormones, gastric inhibitory polypeptide and glucagon-like polypeptide-1(7-36) amide, on fatty acid synthesis in explants of rat adipose tissue," J Endocrinol. 130(2):267-72 (1991).
Office Action issued for Japanese Patent Application No. 2008-509505, mailed on Sep. 6, 2011 (11 pages).
Ørskov et al., "Glucagon-Like peptides GLP-1 and GLP-2, predicted products of the glucagon gene, are secreted separately from pig small intestine but not pancreas," Endocrinology. 119(4):1467-75 (1986).
Pauline et al., "Comparing the Intestinotrophic Effects of 2 Glucagon-Like Peptide-2 Analogues in the Treatment of Short-Bowel Syndrome in Neonatal Piglets," JPEN J Parenter Enteral Nutr. 45(3):538-45 (Mar. 2021).
Petersen et al., "Administration of the protease-resistant glucagon-like peptide 2 analog, [gly2]GLP-2, prior to and concurrently with the chemotherapeutic agent, 5-fluorouracil, inhibits small intestinal atrophy and attenuates bodyweight loss in mice," Gastroenterol. 128(4; Supplement 2): A188 (2005) (1 page).
Pouliot et al., "Follow-up studies on peptic ulcer patients treated with robuden," Can Med Assoc J. 82:524-8 (1960).
Ravis et al., "Pharmacokinetics of insulin following intravenous and subcutaneous administration in canines," Biopharm Drug Dispos. 7(5):407-20 (1986).
Response to Notice of Opposition for European Patent No. 1877435, filed Jun. 25, 2012 (6 pages).
Richter et al., "GLP-1 stimulates secretion of macromolecules from airways and relaxes pulmonary artery," Am J Physiol. 265(4 Pt 1):L374-81 (1993).
Ruiz-Grande et al., "Lipolytic action of glucagon-like peptides in isolated rat adipocytes," Peptides. 13(1):13-6 (1992).
Sasaki et al., "Enteroglucagon, but not CCK, plays an important role in pancreatic hyperplasia after proximal small bowel resection," J Gastroenterol Hepatol. 9(6):576-81 (1994).
Schuster et al., "In Vivo Stability of Therapeutic Proteins," Pharm Res. 37(2):23 (Jan. 2020) (17pages).
Schwartz et al., "Long-Term Teduglutide for the Treatment of Patients With Intestinal Failure Associated With Short Bowel Syndrome," Clin Transl Gastroenterol. 7:e142 (2016) (9 pages).
Sinclair et al., "Proglucagon-derived peptides: mechanisms of action and therapeutic potential," Physiology (Bethesda). 20:357-65 (2005).
Singh et al., "Use of 125I-[Y39]exendin-4 to characterize exendin receptors on dispersed pancreatic acini and gastric chief cells from guinea pig," Regul Pept. 53(1):47-59 (1994).
Skarbaliene et al., "ZP1848, a novel GLP-2 agonist, provides a wide window of therapeutic efficacy in the experimental Crohn's disease model," Gastroenterol. 140(5 Suppl 1):S-519, abstract Su1953 (2011) (1 page).
Submission in opposition proceedings made following summons to attend oral proceedings for European Patent No. 1877435, filed Jan. 13, 2014 (103 pages).
Suda, "The organ distribution and molecular forms of glucagon-related peptides," Yamagata Med J. 6(2):149-161 (1988).
Sørensen et al., "No effect of physiological concentrations of glucagon-like peptide-2 on appetite and energy intake in normal weight subjects," Int J Obes Relat Metab Disord. 27(4):450-6 (Apr. 2003) (9 pages).

(56) References Cited

OTHER PUBLICATIONS

Table filed for European Application No. EP1877435B, on Jan. 14, 2014 (1 page).
Table of selected data from International Application No. 97/39031 filed by P during the oral proceedings of European Patent Application No. EP1877435B on Mar. 13, 2014 (1 page).
Tamaki et al., "Apoptosis in normal tissues induced by anti-cancer drugs," J Int Med Res. 31(1):6-16 (2003).
Tang-Christensen et al., "The proglucagon-derived peptide, glucagon-like peptide-2, is a neurotransmitter involved in the regulation of food intake," Nat Med. 6(7):802-7 (Jul. 2000).
Tavares et al., "Enzymatic- and renal-dependent catabolismof the intestinotropic hormone glucagon-like peptide-2 in rats," Am J Physiol Endocrinol Metab. 278(1):E134-9 (2000).
Thulesen et al., "Glucagon-like peptide 2 (GLP-2) accelerates the growth of colonic neoplasms in mice," Gut. 53(8):1145-50 (2004).
Thymann et al., "Acute effects of the glucagon-like peptide 2 analogue, teduglutide, on intestinal adaptation in short bowel syndrome," J Pediatr Gastroenterol Nutr. 58(6):694-702 (2014).
Torres et al., "Glucagon-like peptide-2 improves both acute and late experimental radiation enteritis in the rat," Int J Radiat Oncol Biol Phys. 69(5):1563-71 (2007).
Valverde et al., "Presence and characterization of glucagon-like peptide-1(7-36) amide receptors in solubilized membranes of rat adipose tissue," Endocrinology. 132(1):75-9 (1993).
Wells, "Additivity of mutational effects in proteins," Biochemistry. 29(37):8509-17 (1990).
Written Opinion of the International Searching Authority from PCT/GB2006/001633, mailed Oct. 24, 2006 (9 pages).
Written Opinion of the International Searching Authority from PCT/GB2007/004273, mailed Apr. 14, 2008 (8 pages).
Wøjdemann et al., "Inhibition of sham feeding-stimulated human gastric acid secretion by glucagon-like peptide-2," J Clin Endocrinol Metab. 84(7):2513-7 (1999).
Yazbeck et al., "Growth factor based therapies and intestinal disease: is glucagon-like peptide-2 the new way forward?," Cytokine Growth Factor Rev. 20(2):175-84 (2009).
Yusta et al., "Enteroendocrine localization of GLP-2 receptor expression in humans and rodents," Gastroenterology. 119(3):744-55 (2000).
Zhu et al., "An updated overview of glucagon-like peptide-2 analog trophic therapy for short bowel syndrome in adults," J Int Med Res. 50(3):3000605221086145 (Mar. 2022) (10 pages).
Reply to Office Action in U.S. Appl. No. 16/511,766, dated Jan. 12, 2023 (7 pages).
Office Action for U.S. Appl. No. 16/511,766, dated Jun. 9, 2023 (29 pages).
Office Action for U.S. Appl. No. 16/511,766, dated Jul. 12, 2022 (25 pages).
Office Action for U.S. Appl. No. 16/511,766, dated Aug. 19, 2021 (22 pages).
Office Action for U.S. Appl. No. 16/511,766, dated May 18, 2020 (26 pages).
Reply to Office Action in U.S. Appl. No. 16/511,766, Feb. 10, 2022 (12 pages).
Reply to Office Action in U.S. Appl. No. 16/511,766, Dec. 8, 2023 (11 pages).
Reply to Office Action in U.S. Appl. No. 16/511,766, dated Sep. 18, 2020 (14 pages).
Reply to Restriction Requirement in U.S. Appl. No. 16/511,766, dated Mar. 27, 2020 (1 page).
Restriction Requirement in U.S. Appl. No. 16/511,766, dated Jan. 30, 2020 (6 pages).
Qiu et al, "Progress on the mechanism of action of glucagon-like peptide 2," Medical Recapitulate. 19(2): 240-242 (Jan. 2013) (6 pages).
Turner et al., "Challenges and Opportunities for the Subcutaneous Delivery of Therapeutic Proteins," available in PMC May 1, 2019, published in final edited form as: J Pharm Sci. 107(5):1247-60 (May 2018) (32 pages).
Lee et al., "Comparison tests for plasma viscosity measurements," International Communications in Heat and Mass Transfer 39:1474-7 (2012).
Wang et al., "Optimization of high-concentration endostatin formulation: Harmonization of excipients' contributions on colloidal and conformational stabilities," Int J Pharm. 530(1-2):173-86 (Sep. 15, 2017).
Extended European Search Report for European Application No. 18197750.5, dated Jul. 5, 2019 (9 pages).
Albericio et al., Chapter 10: Fmoc Methodology: Cleavage from the Resin and Final Deprotection. *Amino Acids, Peptides and Proteins in Organic Chemistry, vol. 3—Building Blocks, Catalysis and Coupling Chemistry*. ed. Andrew B. Hughes, Wiley-VCH Verlag GmbH & Co. KGaA, pp. 349-369 (2010).
Rowe et al., *Handbook of Pharmaceutical Excipients, 6th Edition*. Pharmaceutical Press, 203-205 and 592-594 (2009) (16 pages).
International Search Report for International Application No. PCT/EP2019/076304, mailed Nov. 22, 2019 (6 pages).
International Search Report for International Application No. PCT/EP2019/076305, mailed Nov. 15, 2019 (6 pages).
Naimi et al., "Effects of Short-Term Treatment with Glepaglutide, a Long-Acting Glucagon-Like Peptide-2 Analog, on Intestinal Morphology and Citrulline in Patients with Short Bowel Syndrome," Gastroenterology. 154(6):S-160 (May 2018). Abstract 755.
"Salt Selection and Buffer Preparation—Sigma-Aldrich," Google Search Results, available <https://www.sigmaaldrich.com/US/en/technical-documents/technical-article/protein-biology/protein-concentration-and-buffer-exchange/salt-selection-and-buffer-preparation>, Mar. 17, 2018 (1 page).
Pini et al., "Efficacy and toxicity of the antimicrobial peptide M33 produced with different counter-ions," Amino Acids. 43(1):467-73 (2012).
"Important Biological Buffers," University of Science and Technology of China (USTC). Available <http://staff.ustc.edu.cn/~liuyz/methods/buffer.htm>, May 20, 2016 (1 page).
International Search Report and Written Opinion for International Application No. PCT/EP2022/087440, mailed Apr. 12, 2023 (16 pages).
Written Opinion for International Application No. PCT/EP2019/076305, mailed Nov. 15, 2019 (8 pages).
Lovshin et al., Glucagon-like Peptide 2 (GLP-2), *Encyclopedia of Endocrine Diseases*. ed. Martini, Vo. 2, 225-8 (2004).
Zhu et al., Chapter 11: Formulation of Protein- and Peptide-Based Parenteral Products, *Parenteral Medications, Fourth Edition*. ed. Nema and Ludwig, CRC Press, Boca Raton, 191-217 (Aug. 2019).
Hövelmann et al., "Pharmacokinetic and Pharmacodynamic Characteristics of Dasiglucagon, a Novel Soluble and Stable Glucagon Analog," Diabetes Care. 41(3): 531-37 (Mar. 2018).
Zapadka et al., "Factors affecting the physical stability (aggregation) of peptide therapeutics," Interface Focus. 7(6):20170030 (Dec. 2017) (18 pages).
Extended European Search Report for European Application No. 18197755.4, dated Jul. 5, 2019 (11 pages).
Written Opinion for International Application No. PCT/EP2019/076304, mailed Nov. 22, 2019 (7 pages).
Monbaliu et al., "Recent trends in Cys- and Ser/Thr-based synthetic strategies for the elaboration of peptide constructs," Chem Commun (Camb). 48(95):11601-22 (Dec. 11, 2012).
Cockcroft et al. "Prediction of Creatinine Clearance from Serum Creatinine", Nephron. 16:31-41 (1976).
Nave et al. "Pharmacokinetics of teduglutide in subjects with renal impairment", Eur. J. Clin. Pharmacol. 69(5):1149-1155 (2013).
Levey et al. "Expressing the Modification of Diet in Renal Disease Study Equation for Estimating Glomerular Filtration Rate with Standardized Serum Creatinine Values", Clin Chem. 53(4):766-772 (Apr. 2007).
Guideline on the evaluation of the pharmacokinetics of medicinal products in patients with decreased renal function, European Medicines Agency, 2015 (15 pages).
Guidance for Industry Pharmacokinetics in Patients with Impaired Renal Function—Study Design, Data Analysis, and Impact on

(56) References Cited

OTHER PUBLICATIONS

Dosing, U.S. Department of Health and Human Services, Food and Drug Administration, Center for Drug Evaluation and Research (CDER), Sep. 2020 (19 pages).

Stoeckl et al. "Candidate Reference Methods for Determining Target Values for Cholesterol, Creatinine, Uric Acid, and Glucose in External Quality Assessment and Internal Accuracy Control. I. Method Setup", Clin. Chem. 1993;39:993-1000 (1993).

Costa Geraldes et al., "Protein drug delivery: current dosage form profile and formulation strategies," J Drug Target. 28(4):339-355 (Apr. 2020) (18 pages).

Donald et al., "Salt bridges: geometrically specific, designable interactions," available in PMC Mar. 1, 2012, published in final, edited form as: Proteins. 79(3):898-915 (Mar. 2011) (29 pages).

Falconer, "Advances in liquid formulations of parenteral therapeutic proteins," Biotechnol Adv. 37(7):107412 (Nov. 2019) (9 pages).

Buchman et al., "AGA technical review on short bowel syndrome and intestinal transplantation," Gastroenterology. 124(4):1111-1134 (Apr. 2003).

Pironi et al., "ESPEN guidelines on chronic intestinal failure in adults," Clin Nutr. 35(2):247-307 (Apr. 2016).

Jeppesen et al., "Glepaglutide, a Long-Acting Glucagon-like Peptide-2 Analogue, Reduces Parenteral Support in Patients With Short Bowel Syndrome: A Phase 3 Randomized Controlled Trial," Gastroenterology. Dec. 19, 2024:S0016-5085(24)05787-1 (Dec. 2024).

Larsen et al., "Creating Glepaglutide, the First Long-Acting GLP-2 Analogue to Enable a Ready-to-Use Injection," J Med Chem. (Jan. 2025) (12 pages).

\* cited by examiner

INJECTION PEN FOR SUBCUTANEOUS ADMINISTRATION OF A PEPTIDE

SEQUENCE LISTING

The instant application contains a Sequence Listing which has been submitted electronically in XML file format and is hereby incorporated by reference in its entirety. Said XML copy, created on Oct. 27, 2023, is named "50412-113002_Sequence_Listing_10_27_23" and is 13,892 bytes in size.

FIELD OF THE INVENTION

The present invention relates to injection pens for the subcutaneous administration of a peptide. The present invention further relates to dosage regimes for the administration of glucagon-like-peptide-2 (GLP-2) analogues for inducing longitudinal growth of the intestines, for example for the treatment of patients with short bowel syndrome (SBS). The present invention further relates to medical uses for adjusting the volume of parenteral support (PS) provided to subjects receiving treatment with GLP-2 analogues in response to the treatment and to algorithms for determining PS volume changes.

BACKGROUND OF THE INVENTION

Human GLP-2 is a 33-amino-acid peptide with the following sequence: Hy-His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH (SEQ ID NO: 1). It is derived from specific post-translational processing of proglucagon in the enteroendocrine L cells of the intestine and in specific regions of the brainstem. GLP-2 binds to a single G-protein-coupled receptor belonging to the class II glucagon secretin family.

GLP-2 has been reported to induce significant growth of the small intestinal mucosal epithelium via the stimulation of stem cell proliferation in the crypts, and by inhibition of apoptosis in the villi (Drucker et al., 1996, Proc. Natl. Acad. Sci. USA 93: 7911-7916). GLP-2 also has growth effects on the colon. Furthermore, GLP-2 inhibits gastric emptying and gastric acid secretion (Wojdemann et al., 1999, J. Clin. Endocrinol. Metab. 84: 2513-2517), enhances intestinal barrier function (Benjamin et al., 2000, Gut 47: 112-119), stimulates intestinal hexose transport via the upregulation of glucose transporters (Cheeseman, 1997, Am. J. Physiol. R1965-71), and increases intestinal blood flow (Guan et al., 2003, Gastroenterology, 125: 136-147). A review of GLP-2 and its properties is available in "Glucagon-Like Peptide 2: A Nutrient-Responsive Gut Growth Factor" (Burrin, D G., et al. *The Journal of Nutrition* 131(3): 709-712, 2001).

It has been recognised in the art that glucagon-like peptide-2 receptor analogues have therapeutic potential for the treatment of intestinal diseases. However, the native hGLP-2, a 33 amino acid gastrointestinal peptide, is not a useful in a clinical setting due to its very short half-life in humans of around 7 minutes for full length GLP-2 [1-33] and 27 minutes for truncated GLP-2 [3-33]. In large part, the short half-life is due to degradation by the enzyme dipeptidylpeptidase IV (DPP-IV). Accordingly, there have been attempts in the art to develop GLP-2 receptor agonists with better pharmacokinetic characteristics, in particular to improve the half-life of GLP-2 molecules. By way of example, GLP-2 analogues with substitutions have been suggested such as e.g. GLP-2 analogues containing Gly substitution at position 2 ([hGly2] GLP-2, teduglutide) which increases the half-life from seven minutes (native GLP-2) to about two hours. Acylation of peptide drugs with fatty acid chains has also proven beneficial for prolonging systemic circulation as well as increasing enzymatic stability without disrupting biological potency. However, while these attempts have improved the pharmacokinetics of GLP-2 analogues, and they are sometimes described in the art as "long acting", it must be kept in mind that this is in comparison to native hGLP-2 with half-lives of the order of several hours, rather than minutes. This in turn means that the GLP-2 analogues still need to be administered to patients one or more times per day.

There is considerable interest on the part of patients and healthcare providers in the development of low cost, long-acting, "user-friendly" therapeutic peptides. However, a major difficulty with the delivery of such therapeutic peptides is their short plasma half-life, mainly due to rapid serum clearance and proteolytic degradation via the action of plasma proteases, necessitating frequent, often daily, injections. Patients dislike injections, which leads to reduced compliance and reduced drug efficacy.

WO 2006/117565 (Zealand Pharma A/S) describes GLP-2 analogues which comprise one of more substitutions as compared to [hGly2] GLP-2 and which improved biological activity in vivo and/or improved chemical stability, e.g. as assessed in in vitro stability assays. In particular, GLP-2 analogues are described which have substitutions at one or more of positions 8, 16, 24 and/or 28 of the wild-type GLP-2 sequence, optionally in combination with further substitutions at position 2 and one or more of positions 3, 5, 7, 10 and 11, and/or a deletion of one or more of amino acids 31 to 33. These substitutions may also be combined with the addition of a N-terminal or C-terminal stabilizing peptide sequence. The daily or twice daily administration of these GLP-2 analogues is also described. Among the molecules disclosed in WO 2006/117565 is glepaglutide (ZP1848) which has been designed to be stable in liquid formulations, and is typically administered by daily dosing using an injection pen.

SUMMARY OF THE INVENTION

Broadly, the present invention is based on the surprising finding that the pharmacokinetic (PK) and/or pharmacodynamic (PD) properties of GLP-2 analogues, e.g. of the type disclosed in WO 2006/117565 and WO 2008/056155, enables less frequent administration than has hitherto been proposed. Previous experiments had suggested that GLP-2 analogues, such as ZP1848, had a half-life of about 17 hours which, while being significantly longer than GLP-2 or other GLP-2 analogues, suggested that daily administration ought to be used in the treatment of patients. However, a Phase 2 clinical study in humans using the GLP-2 analogue ZP1848 has now found that the terminal plasma half-life of the molecule is in fact between 5 and 17 days. The terminal plasma half-life is the time required to divide the plasma concentration by two after reaching pseudo-equilibrium. This in turn surprisingly suggests that significantly less frequent dosing of the GLP-2 analogues of the present invention would be efficacious, including weekly and twice weekly dosing. The contents of WO 2006/117565 and WO 2008/056155 are expressly incorporated in their entirety for all purposes, and in particular in relation to the GLP-2 analogues disclosed in these documents.

The results from further studies have also confirmed that both metabolites of ZP1848, i.e. ZP2711 and ZP2469, were present following its administration in vivo and are pharmacologically active, with in vitro potency comparable to ZP1848. The plasma level of ZP2711 is in the same range as that of ZP1848, whereas the plasma level of ZP2469 is multiple times higher than that of ZP1848. Consequently, both metabolites can be included when evaluating systemic exposure as they boths contribute to in vivo efficacy. Due to the high plasma level of ZP2469 this compound has plasma levels above the bioanalytical detection limit (50 pM for ZP2469, 25 pM for ZP1848 and ZP2711), hence it is possible to determine the half-life of compound ZP2469. A terminal plasma half-life of between 5 and 17 days, as shown in the examples, suggests once or twice weekly dosing of ZP1848 would be efficacious.

This in turn enables the administration of the GLP-2 analogues according to the present invention, e.g. once or twice weekly administration. Alternatively or additionally, the dosing regime of the GLP-2 analogues of the present invention may comprise a plurality or course of doses separated in time by 2 days, 2.5 days, 3 days, 3.5 days, 4 days, 5 days, 6 days, 7 days, 8 days, 9 days, 10 days, 11 days or 12 days. In a preferred embodiment, the doses are separated in time by 3 days, 3.5 days, 4 days, 5 days, 6 days, 7 days or 8 days. In a preferred embodiment, doses are separated in time by 3 days, 3.5 days, 4 days or 7 days. As will be appreciated in the art, the time between doses may be varied to some extent so that each and every doses is not separated by precisely the same time. This will often be directed under the discretion of the physician. Thus, doses may be separated in time by a clinically acceptable range of times, e.g. from about 2 days to about 10 days, or from about 3 or 4 days to about 7 or 8 days. The results from the clinical trial that support these conclusions are included in the examples below.

Without being bound by theory, it is presently believed that the unexpected long half-life of the GLP-2 analogues, which enables once or twice weekly dosing, might be obtained due to the combination of the formation of a subcutaneous depot and the formation of metabolites which are slowly released from the subcutaneous depot and which are also agonistic on the GLP-2 receptor. The present inventors believe that the subcutaneous depot is formed on administration of GLP-2 analogues through a reaction between the analogues, i.e. the lysine tail, and with hyaluronic acid in the subcutaneous compartment.

This type of depot has not been seen before for other compounds having a lysine tail, such as lixisenatide which has a half-life of 2-4 hours.

Accordingly, in first aspect, the present invention provides a glucagon-like peptide 2 (GLP-2) analogue for use in a method for the treatment and/or prevention of a stomach and bowel-related disorder in a human patient, wherein the GLP-2 analogue is represented by the formula:

(SEQ ID NO: 11)
$R^1$-$Z^1$-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-$Z^2$-$R^2$ wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In this aspect of the present invention, the glucagon-like peptide 2 (GLP-2) analogue may be used for the treatment and/or prevention of stomach and bowel-related disorders such as ulcers, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemic sprue, enteritis, regional enteritis (Crohn's disease), ulcerative colitis, small intestine damage or short bowel syndrome (SBS). Alternatively or additionally, the glucagon-like peptide 2 (GLP-2) analogue may be used for the treatment and/or prevention of stomach and bowel-related disorders such radiation enteritis, infectious or post-infectious enteritis, or small intestinal damage due to toxic or other chemotherapeutic agents. In this case, treatment with the GLP-2 analogue may optionally be combined with one or more anti-cancer therapies, and may therefore comprise administering one or more chemotherapeutic agent(s) to the patient or treating the patient with radiation therapy.

In a further aspect, the present invention provides a glucagon-like peptide 2 (GLP-2) analogue for use in a method for the treatment and/or prevention of a side effect of chemotherapy or radiation treatment in a human patient, wherein the GLP-2 analogue is represented by the formula:

(SEQ ID NO: 11)
$R^1$-$Z^1$-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-$Z^2$-$R^2$ wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides a glucagon-like peptide 2 (GLP-2) analogue for use in a method for increasing the longitudinal growth of the intestines in a human patient, wherein the GLP-2 analogue is represented by the formula:

(SEQ ID NO: 11)
$R^1$-$Z^1$-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-$Z^2$-$R^2$ wherein:
$R^1$ is hydrogen, $C_{1-4}$ alkyl (e.g. methyl), acetyl, formyl, benzoyl or trifluoroacetyl;
X5 is Ser or Thr;

X11 is Ala or Ser;
R² is NH₂ or OH; and
Z¹ and Z² are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides a glucagon-like peptide 2 (GLP-2) analogue for use in a method for the treatment of short bowel syndrome (SBS) in a human subject receiving a parenteral support (PS) regimen, the method comprising:
(i) administering to the subject a GLP-2 analogue represented by the formula:

(SEQ ID NO: 11)
R¹-Z¹-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-Z²-R² wherein:
R¹ is hydrogen, $C_{1-4}$ alkyl (e.g. methyl), acetyl, formyl, benzoyl or trifluoroacetyl;
X5 is Ser or Thr;
X11 is Ala or Ser;
R² is NH₂ or OH; and
Z¹ and Z² are independently absent or a peptide sequence of 1-6 amino acid units of Lys;
or a pharmaceutically acceptable salt or derivative thereof; and
wherein the GLP-2 analogue is administered once or twice weekly for a time sufficient to lengthen and improve the function of the small intestine of the subject;
(ii) following step (i), reducing a frequency or volume of the parenteral support (PS) regimen in response to improved function of the small intestine; and
(iii) optionally repeating steps (i) and (ii) in response to the subject demonstrating improved function over time as a result of further longitudinal growth of the small intestine.

In a further aspect, the present invention provides a method for the treatment of short bowel syndrome (SBS) in a human subject receiving a parenteral support (PS) regimen, the method comprising:
(i) administering to the subject a GLP-2 analogue represented by the formula:

(SEQ ID NO: 11)
R¹-Z¹-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-Z²-R² wherein:
R¹ is hydrogen, $C_{1-4}$ alkyl (e.g. methyl), acetyl, formyl, benzoyl or trifluoroacetyl;
X5 is Ser or Thr;
X11 is Ala or Ser;
R² is NH₂ or OH; and
Z¹ and Z² are independently absent or a peptide sequence of 1-6 amino acid units of Lys;
or a pharmaceutically acceptable salt or derivative thereof; and
wherein the GLP-2 analogue is administered once or twice weekly for a time sufficient to lengthen and further improve the function of the small intestine of the subject;
(ii) following step (i), reducing a frequency or volume of the parenteral support (PS) regimen in response to improved function of the small intestine; and
(iii) optionally repeating steps (i) and (ii) in response to the subject demonstrating continued improved function of the small intestine.

By way of example, the treatment period over which the GLP-2 analogue is administered to the subject may be from 18 to 150 weeks, for example from 18 to 100 weeks, or from 18 to 52 weeks. However, in other cases where the SBS is a chronic condition, patients may require treatment for the rest of their lives.

In the present context, the term "parenteral support" or "PS" includes the provision of nutrients and/or fluids to the subject receiving GLP-2 therapy as a means of providing the subject with the nutrients and/or fluids that they require, but are unable to absorb fully due to their condition. The determination of the correct amount or volume of PS to provide to subjects with SBS who are receiving GLP-2 therapy is a challenge because if PS volume is not adjusted in a timely and appropriate way, patients may experience fluid overload, are at risk of dehydration and may not achieve optimal clinical responses to the therapy. This is further complicated as the PS volume required by a subject will typically vary during the course of GLP-2 therapy depending on their response to the therapy. Typically, the assessment of the amount of PS volume required by the subject as GLP-2 therapy progresses is dependent on how long the therapy has continued and the responsiveness of individual patients to it. In view of this variation, an initial assessment of PS volume may be carried out within the first few days of GLP-2 therapy, and is typically then followed by a weekly assessment during the first month, a monthly assessment over the next 1-3 months, and thereafter an assessment every 3-6 months until the treatment is concluded. This is important as subjects may experience a rapid initial response to GLP-2 therapy, improving the function of the small intestine, for example even before any increase in the length of the intestine is observed. This in turn enables the PS volume to be reduced, thereby avoiding the risk of side effects, such as fluid overload.

Accordingly, in the above method, step (ii) may include the step of (a) determining the volume of PS required by the subject at that point in the treatment, (b) comparing it to a baseline PS volume determined at the start of therapy with the GLP-2 analogue and (c) reducing the frequency or volume of the PS where the subject demonstrates improved function of the small intestine. Optionally, the reduction of a frequency or volume of the parenteral support (PS) in step (ii) can be performed using the algorithm described below.

By way of illustration of the relationship between the amount of parenteral support required by patients and the degree of improvement in intestinal function, it is presently believed that a 40% increase in length of the small intestine would result in at least a further 10% improvement in function or absorptive capacity of the small intestine. Generally, the GLP-2 therapy according to the present invention leads to improved function or absorptive capacity of the small intestine of at least 10%, more preferably at least 20%, more preferably at least 30% more preferably at least 40%, and most preferably at least 50%. Additionally or alternatively, the amount of the reduction of parenteral support over the course of GLP-2 therapy is at least 10%, more preferably at least 20%, more preferably at least 30%, more preferably at least 40% and most preferably at least 50%. In a preferred embodiment, the reduction of parenteral support is at least 20%.

In a further related aspect, the present invention addresses one of the challenges facing patients and physicians when initiating GLP-2 therapy, namely the appropriate and individualized adjustment in volume of parenteral support (PS) provided to the patient. This is important because if the PS volume is not adjusted in a timely and appropriate way, patients may experience fluid overload, risks of dehydration and may not achieve optimal clinical responses with the therapy.

For example, in a previous 24-week treatment phase 3 study with the GLP-2 analogue teduglutide, an attempt to reduce the parenteral nutrition volume by 10% per month was done at the earliest at week 4 after start of treatment, if the urine output increased by at least 10% from baseline. Many of the patients in this study suffered from fluid overload and stopped drinking (Jeppesen et al. 2011, Gut 2011; 60:902-914). In a follow-up phase 3 study, a 24-week study of SBS patients who were given subcutaneous teduglutide (Jeppesen et al. 2012, Gastroenterology 2012; 143: 1473-1481), the protocol allowed a reduction of parenteral support volume to at least 10%, but not more than 30%, after 2 weeks of treatment, if the urine output increases by at least 10% from baseline. However, in this study, the patients also suffered from fluid overload, in particular at the beginning of the treatment.

Consequently, in this aspect, the present invention enables early assessment of altered PS fluid needs (for example, within a few days of initiating GLP-2 therapy) and provides algorithms for adjusting of PS volume during a course of GLP-2 therapy. It will be appreciated by those skilled in the art that this approach using the algorithm to adjust the PS volume provides a personalised adjustment of the PS volume for each patient. This aspect of the present invention is applicable to GLP-2 therapies using the GLP-2 analogues disclosed herein or using GLP-2 analogues known elsewhere in the art, such as teduglutide.

Accordingly, in a further aspect, the present invention provides a method for adjusting a parenteral support (PS) volume in a human subject receiving an amount or volume of parenteral support each week, the method comprising calculating a new PS volume using an algorithm in which a PS volume for a week is calculated by subtracting seven times the absolute increase in daily urine volume from a baseline volume, i.e. PS volume at the initiation of GLP-2 therapy, from the current weekly volume of parenteral support to provide the new PS volume for the subject. Thus, the new PS volume (weekly) for the subject equals the current PS volume (weekly) minus 7×absolute increase in daily urine volume from the baseline volume.

In a further aspect, the present invention provides a method for determining a parenteral support (PS) volume for a human subject receiving GLP-2 therapy, the method comprising: optionally determining a baseline daily urine volume at the start of GLP-2 therapy; calculating a new PS volume (weekly) for the subject for a coming week based on a current PS volume (weekly) and a daily urine volume (e.g. from a physician visit) using an algorithm in which the new PS volume (weekly) for the subject equals the current PS volume (weekly)−7×absolute increase in daily urine volume from the baseline volume.

In some cases, the calculating step is carried out if the daily urine volume is at least 10% higher than baseline urine volume. This method may comprise the additional step of determining the current PS volume (weekly) for use in the calculation of the new PS volume using the algorithm.

It will be understood that, the method may further comprise the step of administering the PS volume to the subject. Furthermore, the method may be repeated, for example every week, month or at physician visits, enabling the PS volume to be reduced in response to the subject demonstrating continued improved function of the small intestine. In an embodiment, the adjustment of the PS volume results in an urine volume of least 800 ml/day (24 hours), such as at least 1000 ml/day (24 hours) or more. A particular advantage of this method is that the effects of treatment and the consequent adjustment of the PS volume may be carried out very early in the GLP-2 therapy, for example in the first few days of treatment, which is significantly quicker compared to prior art approaches. For example, according to the present invention, subjects may undergo a 0-4 week optimization, followed by a 2-4 weeks stabilization phase. The algorithm for PS volume reductions may be based on changes in urine volume measured during 48 hours.

In some embodiments of this aspect of the present invention, the GLP-2 therapy may comprise administration of a GLP-2 analogue represented by the formula disclosed herein, in particular using the examples of these GLP-2 analogues. In a preferred embodiment the GLP-2 analogue is ZP1848.

Preferably, the method includes the initial steps of determining the baseline volume and/or determining the daily urine volume. Some or all of the steps of the method may be repeated during the course of the GLP-2 therapy received by the subject. Preferably, the first assessment and the determination of changes in the PS volume adjustments is done early in the GLP-2 therapy, such as a few days after the start of the GLP-2 therapy, such as 2, 3, 4, 5, 6, 7 days after start of the GLP-2 therapy. Preferably, the time between repeat testing to determine changes in the PS volume adjustments is initially weekly and later about every 1 to 3 months. For example, in one embodiment, the method may be used at weeks 1, 2, 4, 8 and 12 after commencement of treatment with the GLP-2 analogue, adjusting the PS volume in response to the effects of treatment. The weekly PS volume administered should be monitored and adjusted throughout treatment with the GLP-2 analogue (e.g. glepaglutide) in order to avoid fluid overload. Generally, as the absorptive capacity of the intestines increases after treatment with the GLP-2 analogue, typically by elongation or thickening of the small intestine, the PS volume can be decreased to avoid fluid overload and to improve the treatment needs of the patient.

Other conditions that may be treated with the GLP-2 analogues of the invention, or for which the GLP-2 analogues may be useful prophylactically or therapeutically, include radiation enteritis, infectious or post-infectious enteritis, and small intestinal damage due to toxic or other chemotherapeutic agents. This may require administration of the GLP-2 analogue prior to, concurrently with or following a course of chemotherapy or radiation therapy in order to reduce side effects of chemotherapy such as diarrhoea, abdominal cramping and vomiting, and reduce the consequent structural and functional damage of the intestinal epithelium resulting from the chemotherapy or radiation therapy. Preferably, administration of the GLP-2 analogue according to the invention is initiated 1, 2, 3, 4, 5, 6 or 7 days prior to the initiation of the chemotherapy or radiation cycle. Preferably, administration of the GLP-2 analogue according to the invention is initiated the day before or same day as start of treatment with chemotherapy or radiation cycle and once or twice weekly thereafter.

In a further aspect, the present invention provides the use of a glucagon-like peptide 2 (GLP-2) analogue in the manufacture of a medicament for treating and/or preventing of a stomach and bowel-related disorder in a human patient, wherein the GLP-2 analogue is represented by the formula:

$$R^1-Z^1\text{-His-Gly-Glu-Gly-X5-Phe-Ser-Ser-Glu-Leu-X11-} \\ \text{Thr-Ile-Leu-Asp-Ala-Leu-Ala-Ala-Arg-Asp-Phe-Ile-} \\ \text{Ala-Trp-Leu-Ile-Ala-Thr-Lys-Ile-Thr-Asp-}Z^2-R^2$$
(SEQ ID NO: 11)

wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides the use of a glucagon-like peptide 2 (GLP-2) analogue in the manufacture of a medicament for treating and/or preventing of a side effect of chemotherapy or radiation treatment in a human patient, wherein the GLP-2 analogue is represented by the formula:

$$R^1-Z^1\text{-His-Gly-Glu-Gly-X5-Phe-Ser-Ser-Glu-Leu-X11-} \\ \text{Thr-Ile-Leu-Asp-Ala-Leu-Ala-Ala-Arg-Asp-Phe-Ile-} \\ \text{Ala-Trp-Leu-Ile-Ala-Thr-Lys-Ile-Thr-Asp-}Z^2-R^2$$
(SEQ ID NO: 11)

wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides a method of treating and/or preventing a stomach and bowel-related disorder in a human patient, the method comprising administering to the patient a therapeutically effective amount of glucagon-like peptide 2 (GLP-2) analogue represented by the formula:

$$R^1-Z^1\text{-His-Gly-Glu-Gly-X5-Phe-Ser-Ser-Glu-Leu-X11-} \\ \text{Thr-Ile-Leu-Asp-Ala-Leu-Ala-Ala-Arg-Asp-Phe-Ile-} \\ \text{Ala-Trp-Leu-Ile-Ala-Thr-Lys-Ile-Thr-Asp-}Z^2-R^2$$
(SEQ ID NO: 11)

wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides a method of treating and/or preventing a side effect of chemotherapy or radiation treatment in a human patient, the method comprising administering to the patient a therapeutically effective amount of glucagon-like peptide 2 (GLP-2) analogue represented by the formula:

$$R^1-Z^1\text{-His-Gly-Glu-Gly-X5-Phe-Ser-Ser-Glu-Leu-X11-} \\ \text{Thr-Ile-Leu-Asp-Ala-Leu-Ala-Ala-Arg-Asp-Phe-Ile-} \\ \text{Ala-Trp-Leu-Ile-Ala-Thr-Lys-Ile-Thr-Asp-}Z^2-R^2$$
(SEQ ID NO: 11)

wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides the use of a glucagon-like peptide 2 (GLP-2) analogue in the manufacture of a medicament for increasing the longitudinal growth of the intestines in a human patient, wherein the glucagon-like peptide 2 (GLP-2) analogue represented by the formula:

$$R^1-Z^1\text{-His-Gly-Glu-Gly-X5-Phe-Ser-Ser-Glu-Leu-X11-} \\ \text{Thr-Ile-Leu-Asp-Ala-Leu-Ala-Ala-Arg-Asp-Phe-Ile-} \\ \text{Ala-Trp-Leu-Ile-Ala-Thr-Lys-Ile-Thr-Asp-}Z^2-R^2$$
(SEQ ID NO: 11)

wherein:
$R^1$ is hydrogen, $C_{1-4}$ alkyl (e.g. methyl), acetyl, formyl, benzoyl or trifluoroacetyl;
X5 is Ser or Thr;
X11 is Ala or Ser;
$R^2$ is $NH_2$ or OH; and
$Z^1$ and $Z^2$ are independently absent or a peptide sequence of 1-6 amino acid units of Lys;
or a pharmaceutically acceptable salt or derivative thereof; and
wherein the method comprises administering the GLP-2 analogue to the patient once or twice weekly.

In a further aspect, the present invention provides a method for increasing the longitudinal growth of the intestines in a human patient, the method comprising administering to the patient a therapeutically effective amount of glucagon-like peptide 2 (GLP-2) analogue represented by the formula:

(SEQ ID NO: 11)
R¹-Z¹-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-Z²-R² wherein:
R¹ is hydrogen, $C_{1-4}$ alkyl (e.g. methyl), acetyl, formyl, benzoyl or trifluoroacetyl;
X5 is Ser or Thr;
X11 is Ala or Ser;
R² is $NH_2$ or OH; and
Z¹ and Z² are independently absent or a peptide sequence of 1-6 amino acid units of Lys;
or a pharmaceutically acceptable salt or derivative thereof; and
wherein the method comprises administering the GLP-2 analogue to the patient once or twice weekly.

In all aspects of the present invention, the method of administering the glucagon-like peptide 2 (GLP-2) analogue optionally comprises administering a plurality of doses of the GLP-2 analogue to the patient, wherein the doses are separated in time by one week or half a week. In some cases, it may be desirable to divide a total dose into a plurality (e.g. two or three) separate doses, for example for administration at spaced apart injection sites, for example spacing the injection sites at least 5 cm apart.

Preferably, the doses of the GLP-2 analogues used in accordance with the present invention are in the range between 0.5 mg and 25 mg inclusive per patient once or twice weekly, optionally between 1 mg and 20 mg inclusive per patient once or twice weekly, optionally between 1 mg and 10 mg inclusive per patient once or twice weekly, optionally between 2 mg and 7 mg inclusive per patient once or twice weekly, optionally between 5 mg and 7 mg inclusive per patient once or twice weekly, or optionally between 2 mg and 5 mg inclusive per patient once or twice weekly. In one embodiment, the dose of the GLP-2 analogues used in accordance with the present invention is 10 mg inclusive per patient once or twice weekly. In a course of treatment, the doses taken by the patient may either be the same or different in accordance to the instructions from the physician.

Preferably, the glucagon-like peptide 2 (GLP-2) analogue are administered to patients by injection, most typically by subcutaneous injection or intramuscular injection. In some preferred embodiments, the GLP-2 analogue may be administered using an injection pen, which allow patients to self-administer the analogue. In some aspects, administration of the GLP-2 analogue causes formation of a subcutaneous depot from which the GLP-2 analogue, or metabolites thereof, are released. Without wishing to be bound by any particular explanation, the subcutaneous depot may form through the interaction of the GLP-2 analogues administered in accordance with the present invention, in particular where the analogues comprise a lysine tail (i.e. a Z¹ group and/or a Z² group), through a reaction between the analogues and with hyaluronic acid in the subcutaneous compartment.

In some embodiments of the present invention, in the above formula, X5 is Thr and/or X11 is Ala. Examples of these glucagon-like peptide 2 (GLP-2) analogues include:

ZP1848
(SEQ ID NO: 2)
H-HGEGTFSSELATILDALAARDFIAWLIATKITDKKKKKK-NH₂

ZP2949
(SEQ ID NO: 3)
H-HGEGTFSSELATILDALAARDFIAWLIATKITDKKK-OH

ZP2711
(SEQ ID NO: 4)
H-HGEGTFSSELATILDALAARDFIAWLIATKITDKK-OH

ZP2469
(SEQ ID NO: 5)
H-HGEGTFSSELATILDALAARDFIAWLIATKITDK-OH

ZP1857
(SEQ ID NO: 6)
H-HGEGTFSSELATILDALAARDFIAWLIATKITD-NH₂

ZP2530
(SEQ ID NO: 7)
H-HGEGTFSSELATILDALAARDFIAWLIATKITD-OH

In some embodiments of the present invention, in the above formula X5 is Ser and/or X11 is Ser. Examples of these glucagon-like peptide 2 (GLP-2) analogues include:

ZP1846
(SEQ ID NO: 8)
H-HGEGSFSSELSTILDALAARDFIAWLIATKITDKKKKKK-NH₂

ZP1855
(SEQ ID NO: 9)
H-HGEGSFSSELSTILDALAARDFIAWLIATKITD-NH₂

ZP2242
(SEQ ID NO: 10)
H-HGEGSFSSELSTILDALAARDFIAWLIATKITDK-OH

Embodiments of the present invention will now be described by way of example and not limitation However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION OF THE INVENTION

Definitions

Unless specified otherwise, the following definitions are provided for specific terms, which are used in the above written description.

Throughout the description and claims the conventional one-letter and three-letter codes for natural amino acids are used. All amino acid residues in peptides of the invention are preferably of the L-configuration, However, D-configuration amino acids may also be present.

Preferred compounds of the present invention have at least one GLP-2 biological activity, in particular in causing growth of the intestine. This can be assessed in in vivo assays, for example as described in the examples, in which the mass of the intestine, or a portion thereof is determined after a test animal has been treated or exposed to a GLP-2 analogue.

The GLP-2 analogues of the present invention have one or more amino acid substitutions, deletions, inversions, or additions compared with native GLP-2 and as defined above. This definition also includes the synonym terms GLP-2 mimetics and/or GLP-2 agonists. Further, the analogue of the present invention may additionally have chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Preferably herein lower alkyl is $C_1$-$C_4$ alkyl. Furthermore, one or more side groups, or terminal groups, may be protected by protective groups known to the ordinarily-skilled peptide chemist. The α-carbon of an amino acid may be mono- or di-methylated.

It should be understood that the peptides of the invention might also be provided in the form of a salt or other derivative. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, PA, U.S.A., 1985 and more recent editions, and in the Encyclopaedia of Pharmaceutical Technology.

Other derivatives of the GLP-2 analogues of the invention include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

$Z^1$ and $Z^2$ are independently present and/or absent or a peptide sequence of 1-6 amino acid units of Lys, i.e. 1, 2, 3, 4, 5 or 6 Lys residues. The Lys residues may have either D- or L-configuration, but have an L-configuration. Particularly preferred sequences Z are sequences of four, five or six consecutive lysine residues, and particularly six consecutive lysine residues. Exemplary sequences Z are shown in WO 01/04156. In certain embodiments, $Z^1$ is absent. In such cases, $Z^2$ may be either present or absent.

Pharmaceutical Compositions and Administration

The GLP-2 analogues of the present invention, or salts or derivatives thereof, may be formulated as pharmaceutical compositions prepared for storage or administration, and which comprise a therapeutically effective amount of a GLP-2 peptide of the present invention, or a salt or derivative thereof, in a pharmaceutically acceptable carrier. In accordance with the dosage regimes of the present invention, the GLP-2 analogues are adminstered to patients, e.g. a human patient, once or twice weekly. Thus, a course of administration according to the present invention may entail administering to a patient a course of doses separated in time by 2 days, 2.5 days, 3 days, 3.5 days, 4 days, 5 days, 6 days, 7 days, 8 days, 9 days, 10 days, 11 days, 12 days, 13 days or 14 days, and more preferably separated in time by 3 days, 4 days, 5 days, 6 days, 7 days or 8 days. In some specific situations, the present invention may entail administering to a patient a fixed dose of e.g. 10 mg once or twice weekly.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy so as to deliver the peptide to the large intestine, but will depend on such factors as weight, diet, concurrent medication and other factors, well known those skilled in the medical arts.

It is within the invention to provide a pharmaceutical composition, wherein the GLP-2 analogue, or a salt thereof is present in an amount effective to treat or prevent stomach and bowel-related disorders or to induce longitudinal growth of the intestines.

Pharmaceutically acceptable salts of the compounds of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalensulfonic, benzenesulfonic, toluenesulfonic, and camphorsulfonic as well as other known pharmaceutically acceptable acids. Amino acid addition salts can also be formed with amino acids such as lysine, glycine, or phenylalanine.

As is apparent to one skilled in the medical art, a "therapeutically effective amount" of the peptides or pharmaceutical compositions of the present invention will vary depending upon the age, weight and mammalian species treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of preventing and/or treating the intestine and stomach related diseases described herein, as well as other medical indications disclosed herein, to inducing longitudinal growth of the intestines, will be within the ambit of the skilled person.

As used herein, "a therapeutically effective amount" is one which reduces symptoms of a given condition or pathology, and preferably which normalizes physiological responses in an individual with the condition or pathology. Reduction of symptoms or normalization of physiological responses can be determined using methods routine in the art and may vary with a given condition or pathology. In one aspect, a therapeutically effective amount of one or more GLP-2 analogues or pharmaceutical composition comprising the one or more GLP-2 analogues is an amount which restores a measurable physiological parameter to substantially the same value (preferably to within +30%, more preferably to within +20%, and still more preferably, to within 10% of the value) of the parameter in an individual without the condition or pathology.

In one embodiment of the invention administration of the compounds or pharmaceutical composition of the present invention is commenced at lower dosage levels, with dosage levels being increased until the desired effect of preventing/treating the relevant medical indication, such as intestine and stomach related diseases or increased longitudinal growth of the intestines, is achieved. This would define a therapeutically effective amount. Whether alone or as part of a pharmaceutical composition, the doses of the GLP-2 analogues used in accordance with the present invention are typically in the range between 0.5 mg and 25 mg inclusive per patient once or twice weekly, optionally between 1 mg and 20 mg inclusive per patient once or twice weekly, optionally between 1 mg and 10 mg inclusive per patient once or twice weekly, optionally between 2 mg and 7 mg inclusive per patient once or twice weekly, optionally between 5 mg and 7 mg inclusive per patient once or twice weekly, or optionally between 2 mg and 5 mg inclusive per patient once or twice weekly. In one embodiment, a therapeutically effective amount of the GLP-2 analogues used in accordance with the present invention is about 10 mg per patient once or twice weekly. However, the skilled person will be able to adjust these doses in the event that an alternative dosing regime in accordance with the disclosure herein is selected.

In aspects of the invention relating to achieving increased longitudinal growth of the intestines, preferably treatment with the GLP-2 analogues of the present invention increases intestinal growth by at least 30% compared to the control, more preferably by at least 40% compared to the control, and most preferably by at least 50% compared to the control. It is generally preferred that the increase in longitudinal growth is accompanied by increased of absorptive capacity during and to some extent even after treatment has stopped. In the treatment of human patient at need to gaining increased longitudinal growth of the intestines, such as patients with short bowl syndrome (SBS), generally the treatment will last for at least 1 to 3 years and may optionally entail treatment once or twice weekly or in accordance with another of the treatment regimes of the present invention described herein.

The class of human patients with SBS includes patients having SBS-intestinal failure (SBS-IF) and patients who are on the border between having SBS-intestinal insufficiency (SBS-II) and SBS-intestinal failure (SBS-IF). In some cases, patients having SBS-intestinal failure (SBS-IF) are also called SBS-PS when they are dependent on parenteral support, and the patients having SBS-intestinal insufficiency (SBS-II) are also called SBS non-PS if they are not depending on parenteral support.

The spectrum of patient types with SBS is reviewed in Jeppensen, Journal of Parenteral and Enteral Nutrition, 38(1), 8S-13S, May 2014, doi: 10.1177/0148607114520994. A further division of SBS patient types can be made along the lines described in Schwartz et al., Clinical and Translational Gastroenterology (2016) 7, e142; doi:10.1038/ctg.2015.69. This separates SBS patients into early responders and late/slow responders. Without being bound by theory, the present inventors believe that the early responders are the ones who exhibit an early effect on treatment with a GLP-2 analogue caused by, among other effects, an increase in the width/diameter of the small intestine, while the late or slow responders are the patients which mostly or first benefit to the treatment with a GLP-2 analogue caused by an increase in the length of the small intestine. The determination of whether a subject is an early or a late responder may be used to determine the duration of the treatment regime with the GLP-2 analogue, the timing of any clinical decision to reduce parenteral support and the interval between testing to determine whether a reduction in parenteral support is possible. Accordingly, in one embodiment, the patient is a late or slow responder. The length of the small intestines may for example be measured by CT scan (computed tomography scan), MRI (magnetic resonance imaging), histology, laparoscopic or other measurements or techniques known in the art.

In a further aspect, the present invention provides a glucagon-like peptide 2 (GLP-2) analogue for use in a method for the treatment and/or prevention of a patient having SBS-intestinal insufficiency (SBS-II), wherein the treatment prevents or delays the development of SBS-intestinal failure (SBS-IF), wherein the GLP-2 analogue is represented by the formula:

(SEQ ID NO: 11)
$R^1$-$Z^1$-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-$Z^2$-$R^2$ wherein:

$R^1$ is hydrogen, $C_{1-4}$ alkyl (e.g. methyl), acetyl, formyl, benzoyl or trifluoroacetyl; and X5 is Ser or Thr;

X11 is Ala or Ser;

$R^2$ is $NH_2$ or OH; and $Z^1$ and $Z^2$ are independently absent or a peptide sequence of 1-6 amino acid units of Lys;

or a pharmaceutically acceptable salt or derivative thereof.

In some embodiments, the method may comprise administering the GLP-2 analogue to the patient once or twice weekly and/or according to any of the other treatment regimes described herein.

In other related aspects, the present invention provides the use of a GLP-2 analogue is represented by the formula:

```
                                              (SEQ ID NO: 11)
R¹-Z¹-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-Z²-R²
``` wherein:
R¹ is hydrogen, $C_{1-4}$ alkyl (e.g. methyl), acetyl, formyl, benzoyl or trifluoroacetyl;
X5 is Ser or Thr;
X11 is Ala or Ser;
R² is $NH_2$ or OH; and
$Z^1$ and $Z^2$ are independently absent or a peptide sequence of 1-6 amino acid units of Lys;
or a pharmaceutically acceptable salt or derivative thereof, for the manufacture of a medicament for the treatment and/or prevention of a patient having SBS-intestinal insufficiency (SBS-II), wherein the treatment prevents or delays the development of SBS-intestinal failure (SBS-IF).

In other related aspects, the present invention provides a method for treating and/or preventing of a patient having SBS-intestinal insufficiency, wherein the method prevents or delays the development of SBS-intestinal failure, wherein the GLP-2 analogue is represented by the formula:

```
                                              (SEQ ID NO: 11)
R¹-Z¹-His-Gly-Glu-Gly-X5-Phe-Ser-Ser-Glu-Leu-X11-

Thr-Ile-Leu-Asp-Ala-Leu-Ala-Ala-Arg-Asp-Phe-Ile-

Ala-Trp-Leu-Ile-Ala-Thr-Lys-Ile-Thr-Asp-Z²-R²
``` wherein:
R¹ is hydrogen, $C_{1-4}$ alkyl (e.g. methyl), acetyl, formyl, benzoyl or trifluoroacetyl;
X5 is Ser or Thr;
X11 is Ala or Ser;
R² is $NH_2$ or OH; and
$Z^1$ and $Z^2$ are independently absent or a peptide sequence of 1-6 amino acid units of Lys;
or a pharmaceutically acceptable salt or derivative thereof.

For therapeutic use, the chosen GLP-2 analogue is formulated with a carrier that is pharmaceutically acceptable and is appropriate for delivering the peptide by the chosen route of administration. For the purpose of the present invention, peripheral parenteral routes include intravenous, intramuscular, subcutaneous, and intraperitoneal routes of administration. In one embodiment, the route of administration is the subcutaneous route or subcutaneous administration. The present pharmaceutical composition comprises a GLP-2 analogue of the invention, or a salt or derivative thereof and a pharmaceutically acceptable carrier. Suitable pharmaceutically acceptable carriers are those used conventionally with peptide-based drugs, such as diluents, excipients and the like. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges are pH 4-8, pH 6.5-8, more preferably pH 7-7.5. Preservatives, such as para, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers, preventing oxidation, deamidation, isomerisation, racemisation, cyclisation, peptide hydrolysis, such as e.g. ascorbic acid, methionine, tryptophane, EDTA, asparagine, lysine, arginine, glutamine and glycine may be provided in the pharmaceutical composition. Stabilizers, preventing aggregation, fibrillation and precipitation, such as Sodium dodecyl sulphate, polyethylene glycol, carboxymethyl cellulose, cyclodextrine may be provided in the pharmaceutical composition. Organic modifiers for solubilization or preventing aggregation, such as ethanol, acetic acid or acetate and salts thereof may be provided in the pharmaceutical composition. Isotonicity makers such as salts e.g. sodium chloride or most preferred carbohydrates e.g. dextrose, mannitol, lactose, trehalose, sucrose or mixtures thereof may be provided in the pharmaceutical composition.

Detergents, such as Tween 20, Tween 80, SDS, Poloxamers e.g. Pluronic F-68, Pluronic F-127, may be provided in the pharmaceutical composition. Dyes and even flavoring agents may be provided in the pharmaceutical composition. In another embodiment, a pharmaceutically acceptable acid addition salt of the GLP-2 peptide analogue is provided for. Suspending agents may be used.

Organic modifiers, such as ethanol, tertiary-buthanol, 2-propanol, ethanol, glycerol, Polyethylene glycol may be provided in the pharmaceutical formulation for lyophilization of a lyophilized product. Bulking agents and isotonicity makers such as salt e.g. sodium chloride, carbohydrates e.g. dextrose, mannitol, lactose, trehalose, sucrose or mixtures thereof, aminoacids e.g. glycine, glutamate, or excipients such as cystein, lecithin or human serum albumin, or mixtures thereof may be provided in the pharmaceutical composition for lyophilization.

The pharmaceutical compositions of the present invention may be formulated and used as tablets, capsules or elixirs for oral administration; suppositories for rectal administration; preferably sterile solutions or sterile powder or suspensions for injectable administration; and the like. The dose and method of administration can be tailored to achieve optimal efficacy but will depend on such factors as weight, diet, concurrent medication and other factors, which those skilled in the medical arts will recognize.

When administration is to be parenteral, such as intravenous, subcutaneous or intramuscular injectable pharmaceutical compositions can be prepared in conventional forms, either as aqueous solutions or suspensions; lyophilized, solid forms suitable for reconstitution immediately before use or suspension in liquid prior to injection, or as emulsions.

Diluents for reconstitution of the lyophilized product may be a suitable buffer from the list above, water, saline, dextrose, mannitol, lactose, trehalose, sucrose, lecithin, albumin, sodium glutamate, cysteine hydrochloride; or water for injection with addition of detergents, such as Tween 20, Tween 80, poloxamers e.g. pluronic F-68 or pluronic F-127, polyethylene glycol, and or with addition of preservatives such as para-, meta-, and ortho-cresol, methyl- and propylparaben, phenol, benzyl alcohol, sodium benzoate, benzoic acid, benzyl-benzoate, sorbic acid, propanoic acid, esters of p-hydroxybenzoic acid, and or with addition of an organic modifier such as ethanol, acetic acid, citric acid, lactic acid or salts thereof.

In addition, if desired, the injectable pharmaceutical compositions may contain minor amounts of non-toxic auxiliary substances, such as wetting agents, or pH buffering agents. Absorption enhancing preparations (e.g., liposomes, detergents and organic acids) may be utilized.

In one embodiment of the invention, the compounds are formulated for administration by infusion, e.g., when used as liquid nutritional supplements for patients on total parenteral nutrition therapy (for example neonatals, or patients suffering from cachexia or anorexia), or by injection, for example subcutaneously, intraperitoneal or intravenously, and are accordingly utilized as aqueous solutions in sterile and pyrogen-free form and optionally buffered to physiologically tolerable pH, e.g., a slightly acidic or physiological pH. Formulation for intramuscular administration may be based on solutions or suspensions in plant oil, e.g. canola oil, corn oil or soy bean oil. These oil based formulations may be stabilized by antioxidants e.g. BHA (butylated hydroxianisole) and BHT (butylated hydroxytoluene).

Thus, the present peptide compounds may be administered in a vehicle, such as distilled water or in saline, phosphate buffered saline, 5% dextrose solutions or oils. The solubility of the GLP-2 analogue may be enhanced, if desired, by incorporating a solubility enhancer, such as detergents and emulsifiers.

The aqueous carrier or vehicle can be supplemented for use as injectables with an amount of gelatin that serves to depot the GLP-2 analogue at or near the site of injection, for its slow release to the desired site of action. Alternative gelling agents, such as hyaluronic acid, may also be useful as depot agents.

In one embodiment of the present invention the formulation comprises
  a. L-histidine dissolved in water to obtain final concentrations of from 0.5 mM to 300 mM, preferably from 3 to 200 mM, most preferably from 20 to 100 mM;
  b. mannitol to obtain up to 350 mM, preferably from 30 to 300 mM, most preferably from 100 mM to 230 mM; and
  c. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In another embodiment of the present invention the formulation comprises
  a. L-histidine dissolved in water to obtain final concentrations of from 0.5 mM to 300 mM, preferably from 3 to 200 mM, most preferably from 20 to 100 mM L-histidine;
  b. L-Arginine to obtain up to 200 mM, preferably from 0.5 to 100 mM, most preferably from 5 to 50 mM;
  c. mannitol to obtain up to 350 mM, preferably from 30 to 300 mM, most preferably from 100 mM to 230 mM; and
  d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In still another embodiment of the present invention the formulation comprises
  a. L-histidine dissolved in water to obtain final concentrations of up to 200 mM, preferably from 3 to 100 mM, most preferably from 5 to 50 mM L-histidine;
  b. L-Arginine to obtain up to 200 mM, preferably from 0.5 to 100 mM, most preferably from 5 to 50 mM;
  c. mannitol to obtain up to 350 mM, preferably from 30 to 300 mM, most preferably from 100 mM to 230 mM; and
  d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
  a. N-acetate dissolved in water to obtain final concentrations of from up to 200 mM, preferably from 0.5 to 100 mM, most preferably from 5 to 50 mM L-histidine;
  b. mannitol to obtain up to 350 mM, preferably from 30 to 300 mM, most preferably from 100 mM to 230 mM.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product The GLP-2 analogues of the invention may also be formulated as a slow release implantation device for extended and sustained administration of the GLP-2 peptide analogue. Such sustained release formulations may be in the form of a patch positioned externally on the body. Examples of sustained release formulations include composites of biocompatible polymers, such as poly(lactic acid), poly(lactic-co-glycolic acid), methylcellulose, hyaluronic acid, sialic acid, silicate, collagen, liposomes and the like. Sustained release formulations may be of particular interest when it is desirable to provide a high local concentration of a GLP-2 analogue of the invention.

The GLP-2 analogue may be utilized in the form of a sterile-filled vial or ampoule containing an intestinotrophic amount of the peptide, in either unit dose or multi-dose amounts. The vial or ampoule may contain the GLP-2 analogue and the desired carrier, as an administration ready formulation. Alternatively, the vial or ampoule may contain the GLP-2 peptide in a form, such as a lyophilized form, suitable for reconstitution in a suitable carrier, such as sterile water or phosphate-buffered saline.

The peptide compounds of the present invention may be used alone, or in combination with compounds having an anti-inflammatory effect. Without being bound by theory it is envisioned that such combination treatment may enforce the beneficial treatment effects of the present peptide analogues.

The therapeutic dosing and regimen most appropriate for patient treatment will of course vary with the disease or condition to be treated, and according to the patient parameters. Without wishing to be bound by any particular theory, it is expected that doses, between 0.1 and 25 mg per patient, and shorter or longer duration or frequency of treatment may produce therapeutically useful results, such as a statistically significant increase particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in further clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

A human dose of a GLP-2 peptide according to the invention may be used in a dose of between about 0.01 mg/kg and 100 mg/kg body weight, such as between about 0.01 mg/kg and 10 mg/kg body weight, for example between 10-100 g/kg body weight. In further embodiments, a human dose (total dose) of a GLP-2 peptide according to the invention may be from about such as between and including 0.1 mg and 25 mg per patient between and including 0.5 mg and 20 mg per patient, such as between and including 1 mg and 15 mg per patient, such as between and including 1 mg and 10 mg per patient once or twice weekly or as a plurality of doses as defined herein separated in time by 2, 3, 4, 5, 6, 7, 8, 9, 10, 11, 12, 13 or 14 days. In some instances, a fixed dose of the GLP-2 peptide according to the invention may be used in accordance with a dosing pattern disclosed herein, i.e. a dose which is the same regardless of the body weight of the patient, given once or twice weekly. By way of example, the fixed dose may be a dose of 5 mg, 6 mg, 7 mg, 8 mg, 9, mg, 10 mg, 11 mg, 12 mg, 13 mg, 14 mg or 15 mg. Conveniently a fixed dose of 10 mg may be used. The use of fixed dosing has the advantage of increasing compliance and reducing the risk of patient dosing errors, including risks of miscalculating a weight based dose to be administered.

Medical Conditions

The peptides of the present invention are useful as a pharmaceutical agent for preventing or treating an individual suffering from gastro-intestinal disorders, including the upper gastrointestinal tract of the oesophagus by administering an effective amount of a GLP-2 analogue, or a salt thereof as described herein. The stomach and intestinal-related disorders include ulcers of any aetiology (e.g., peptide ulcers, drug-induced ulcers, ulcers related to infections or other pathogens), digestion disorders, malabsorption syndromes, short-bowel syndrome, cul-de-sac syndrome, inflammatory bowel disease, celiac sprue (for example arising from gluten induced enteropathy or celiac disease), tropical sprue, hypogammaglobulinemic sprue, enteritis, ulcerative colitis, small intestine damage, and chemotherapy induced diarrhea/mucositis (CID).

As mentioned above in general, individuals who would benefit from increased small intestinal mass and consequent and/or maintenance of normal small intestine mucosal structure and function are candidates for treatment with the present GLP-2 analogues. Particular conditions that may be treated with GLP-2 analogue include the various forms of sprue including celiac sprue which results from a toxic reaction to alpha-gliadin from heat and may be a result of gluten-induced enteropathy or celiac disease, and is marked by a significant loss of villae of the small bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 analogue treatment may be monitored by enteric biopsy to examine the villus morphology, by biochemical assessment of nutrient absorption, by patient weight gain, or by amelioration of the symptoms associated with these conditions.

Another particular condition which may be treated with the GLP-2 analogues of the invention, or for which the GLP-2 analogues may be useful therapeutically and/or prophylactically is short bowel syndrome (SBS), also known as short gut syndrome or simply short gut) which results from surgical resection, congenital defect or disease-associated loss of absorption in the bowel in which patients are subsequently unable to maintain fluid, electrolyte, and nutrient balances on a conventional diet. Despite an adaptation that occurs generally in the two years after resection, SBS patients have reduced dietary uptake and fluid loss.

Other conditions that may be treated with the GLP-2 analogues of the invention, or for which the GLP-2 analogues may be useful prophylactically, include in addition to the above mentioned radiation enteritis, infectious or post-infectious enteritis, and small intestinal damage due to cancer-chemotherapeutic or toxic agents.

The GLP-2 analogues may also be used for the treatment of malnutrition, for example cachexia and anorexia.

A particular embodiment of the invention is concerned with using the present peptides for the prevention and/or treatment of intestinal damage and dysfunction. Such damage and dysfunction is a well-known side effect of cancer-chemotherapy treatment. Chemotherapy administration is frequently associated with unwanted side effects related to the gastrointestinal system such as mucositis, diarrhoea, bacterial translocation, malabsorption, abdominal cramping, gastrointestinal bleeding and vomiting. These side effects are clinical consequences of the structural and functional damage of the intestinal epithelium and frequently make it necessary to decrease the dose and frequency of chemotherapy. Administration of the present GLP-2 peptide analogues may enhance trophic effect in the intestinal crypts and rapidly provide new cells to replace the damaged intestinal epithelium following chemotherapy. The ultimate goal achieved by administering the present peptides is to reduce the morbidity related to gastrointestinal damage of patients undergoing chemotherapy treatment while creating the most optimal chemotherapy regime for the treatment of cancer. Concomitant prophylactic or therapeutic treatment may be provided in accordance with the present invention to patients undergoing or about to undergo radiation therapy.

The stem cells of the small intestinal mucosa are particularly susceptible to the cytotoxic effects of chemotherapy due to their rapid rate of proliferation (Keefe et al., Gut 2000; 47: 632-7). Chemotherapy-induced damage to the small intestinal mucosa is clinically often referred to as gastrointestinal mucositis and is characterized by absorptive and barrier impairments of the small intestine. For example, it has been shown that, the broadly used chemotherapeutic agents, 5-FU, irinotecan and methothrexate increase apoptosis leading to villus atrophy and crypt hypoplasia in the small intestine of rodents (Keefe et al., Gut 47: 632-7, 2000; Gibson et al., J Gastroenterol Hepatol. September; 18(9): 1095-1100, 2003; Tamaki et al., J Int Med Res. 31(1):6-16, 2003). Chemotherapeutic agents have been shown to increase apoptosis in intestinal crypts at 24 hours after administration and subsequently to decrease villus area, crypt length, mitotic count per crypt, and enterocyte height three days after chemotherapy in humans (Keefe et al., Gut 2000; 47: 632-7). Thus, structural changes within the small intestine directly lead to intestinal dysfunction and in some cases diarrhea.

Gastrointestinal mucositis after cancer chemotherapy is an increasing problem that is essentially untreatable once established, although it gradually remits. Studies conducted with the commonly used cytostatic cancer drugs 5-FU and irinotecan have demonstrated that effective chemotherapy with these drugs predominantly affects structural integrity and function of the small intestine while the colon is less sensitive and mainly responds with increased mucus formation (Gibson et al., J Gastroenterol Hepatol. September; 18(9):1095-1100, 2003; Tamaki et al., J Int Med Res. 31(1):6-16, 2003).

The novel GLP-2 analogues of the present invention may be useful in the prevention and/or treatment of gastrointestinal injury and side effects of chemotherapeutic agents. This potentially important therapeutic application may apply to currently used chemotherapeutic agents such as but not limited to: 5-FU, Altretamine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/ Thioguanine, Topotecan, Treosulfan, Vinblastine, Vincristine, Vindesine, Vinorelbine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, and Vinorelbine.

A further embodiment of the invention is concerned with using the present peptides for increasing the longitudinal growth of the intestines in a patient, e.g. in a human patient. As shown in the Examples below, the GLP-2 analogues of the invention are capable of increasing the longitudinal growth of the intestines relative to the control. Without being bound by theory, it is presently believed that the longer half-life leads to a more potent and prolonged stimulation of the GLP-2 receptors which results in an increased longitudinal growth relative to that of the control. It is also possible that the longer terminal plasma half-life of the GLP-2 analogues used in accordance with the present invention leads to more potent stimulation of longitudinal growth of the intestines as compared to other GLP-2 analogues of the prior art known to have relatively shorter half-lives.

This capability is of particular value in patients with SBS as this will lead to increased absorptive capacity also after treatment is stopped. Such patient would be treated for at least 1 to 3 years, such as at least 1 to 4 years, such as 1 to 10 years, such as 1 to 20 years, such as 1 to 35 years with the objective of inducing longitudinal growth of the intestines.

As already described herein, SBS patients who are on the border between intestinal insufficiency (SBS-II) or SBS-PS patients and intestinal failure (SBS-IF) or SBS non-PS may therefore have particular value from having their intestines lengthened over a 1 to 3 year treatment course, whereafter their risk if intestinal failure is decreased, for example involving weekly or twice weekly dosing over the period of treatment. This involves less risk for central catheter needs and the risk of sepsis associated with its use.

The dosages regimes disclosed herein may be applied to the treatment of stomach and bowel-related disorders, such as SBS, in which the subject of the treatment is provided with parenteral support (PS) while receiving treatment with the GLP-2 analogues according to the present invention. Parenteral support involves the administration of nutrition and liquid to patients whose gastrointestinal tract is impaired or compromised, while they are being treated with GLP-2 analogues. However, one of the challenges facing patients and physicians in the course of GLP-2 therapy concerns the determination of the amount or the volume of PS provided to the treated subject and the appropriate and individualized adjustment of the amount or the volume of PS provided to the patient. In particular, this is important because if the amount or the volume PS is not adjusted in an appropriate way, the treated subjects may experience fluid overload, risks of dehydration and may not achieve optimal clinical responses with the therapy. Consequently, the present invention provides algorithms for adjusting of the amount or the volume PS during a course of treatment using a GLP-2 analogue as disclosed herein.

Accordingly, in a further treatment related aspect, the present invention provides a glucagon-like peptide 2 (GLP-2) analogue for use in a method for the treatment of short bowel syndrome (SBS) in a human subject receiving a parenteral support (PS) regimen, the method comprising:
  (i) administering to the subject a GLP-2 analogue as defined herein, wherein the GLP-2 analogue is administered once or twice weekly for a period of time sufficient to lengthen and improve the function of the small intestine of the subject; and
  (ii) following step (i), reducing a frequency or amount of the parenteral support (PS) regimen in response to improved function of the small intestine.
  (iii) optionally repeating steps (i) and (ii) in response to the subject demonstrating continued improved function of the small intestine.

By way of example, the time interval over which the GLP-2 analogue is administered in step (i) of the method is from 18 to 150 weeks, for 18 to 100 weeks, or for 18 to 52 weeks. Generally, the amount of improved function or absorptive capacity of the small intestine is at least 10%, such as at least 20%, such as at least 30% such as at least 40%, such as at least 50%. Additionally or alternatively, the amount of the reduction of parenteral support is at least 10%, at least 20%, at least 30%, at least 40% or at least 50%. In a preferred embodiment, the reduction of parenteral support is at least 20%.

In order to assist with the determination of the amount or the volume of PS provided to subjects receiving GLP-2 therapy, in a further aspect, the present invention provides a method for adjusting a parenteral support (PS) in a human subject receiving an amount or volume of parenteral support each week, the method comprising calculating a new amount or volume of PS using an algorithm in which an amount or volume of PS for a week is calculated by subtracting seven times the absolute increase in daily urine volume from a baseline from the current weekly volume of parenteral support to provide the new amount or volume of PS for the subject. Preferably, the method includes the initial steps of determining the baseline volume and/or determining the daily urine volume. Some or all of the steps of the method may be repeated during the course of the GLP-2 therapy received by the subject. Preferably, the time between repeat testing to determine changes in the PS volume adjustments is about every 1 to 3 months. For example, in one embodiment, the method may be used at weeks 1, 2, 4, 8 and 12 after commencement of treatment with the GLP-2 analogue, adjusting the amount or volume of PS in response to the effects of treatment. The weekly amount or volume of PS administered should be monitored and adjusted throughout treatment with the GLP-2 analogue (e.g. glepaglutide) in order to avoid fluid overload. Generally, as the absorptive capacity of the intestines increases after treatment with the GLP-2 analogue, typically by elongation or thickening of the small intestine, the amount or volume of PS can be decreased to avoid fluid overload and to improve the treatment needs of the patient.

EXAMPLES

The following examples are provided to illustrate preferred aspects of the invention and are not intended to limit the scope of the invention. The GLP-2 analogues administered according to the dosage regimes described herein can be made according to the methods such as solid phase peptide synthesis described in WO 2006/117565, the content of which is expressly incorporated by reference in its entirety.

Example 1. Synthesis of ZP1848 Metabolites

Solid phase peptide synthesis was performed on a CEM Liberty Peptide Synthesizer using standard Fmoc chemistry. TentaGel S Ram S resin (1.33 g; 0.25 mmol/g) was swelled in DMF (10 ml) prior to use and transferred between tube and reaction vessel using DCM and DMF.
Coupling
An Fmoc-amino acid in DMF/DCM (2:1; 0.2 M; 5 ml) was added to the resin in a CEM Discover microwave unit together with COMU/DMF (0.5 M; 2 ml) and DIPEA&DMF (2.0 M; 1 ml). The coupling mixture was heated to 75° C. for 5 min while nitrogen was bubbled through the mixture. The resin was then washed with DMF (4×10 ml). Fmoc-Phe-Ser(Psi Me,Me,Pro)-OH pseudoproline was used for amino acid number six and seven.
Deprotection Piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).

The resin was washed with EtOH (3×10 ml) and Et2O (3×10 ml) and dried to constant weight at room temperature (r.t.). The crude peptide was cleaved from the resin by treatment with TFA/DODT (95/5; 60 ml, 2 h; r.t.). Most of the TFA was removed at reduced pressure and the crude peptide was precipitated and washed three times with diethylether and dried to constant weight at room temperature.
HPLC Purification of the Crude Peptide The crude peptide was first purified to 45% by preparative reverse phase HPLC using a PerSeptive Biosystems VISION Workstation equipped with a Gemini NX 5μ C-18 110A, 10×250 mm column and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The product (143 mg) was purified a second time with a C4 Jupiter 2, 12×25 cm column, to yield 27 mg, with a purity of 89% as characterized by HPLC and MS. Calculated monoisotopic MW=3377.61, found 3377.57.

TABLE 1

Synthesized compounds

| Compound | Sequence | SEQ ID NO: |
|---|---|---|
| Teduglutide | H-HGDGSFSDEMNTILDNLAARDFINWLIQTKI TD-OH | 1 |
| ZP1848 | H-HGEGTFSSELATILDALAARDFIAWLIATKI TDKKKKKK-NH$_2$ | 2 |
| ZP2949 | H-HGEGTFSSELATILDALAARDFIAWLIATKI TDKKK-OH | 3 |
| ZP2711 | H-HGEGTFSSELATILDALAARDFIAWLIATKI TDKK-OH | 4 |
| ZP2469 | H-HGEGTFSSELATILDALAARDFIAWLIATKI TDK-OH | 5 |

Example 2. GLP-2R EC50 Measurements

Generation of Cell Line Expressing Human GLP-2 Receptors

The hGLP2-R was purchased from MRC-geneservice, Babraham, Cambridge as an Image clone: 5363415 (11924-117). For subcloning into a mammalian expression vector, primers for subcloning were obtained from DNA-Technology, Risskov, Denmark. The 5' and 3' primers used for the PCR reaction include terminal restriction sites for cloning and the context of the 5' primer is modified to a Kozak consensus without changing the sequence of the product encoded by the ORF. A standard PCR reaction was run using Image clone 5363415 (11924-117) as a template with the above mentioned primers and Polymerase Herculase II Fusion in a total vol. of 50 μl. The generated PCR product was purified using GFX PCR and Gel band purification kit, digested with restriction enzymes and cloned into the mammalian expression vector using Rapid DNA Ligation Kit. Ligation reaction was transformed to XL10 Gold Ultracompetent cells and colonies were picked for DNA production using Endofree Plasmid maxi kit. Subsequent sequence analysis was conducted by MWG Eurofins, Germany. The clone was confirmed to be the hGLP-2 receptor, splice variant rs17681684.

HEK293 cells were transfected using the Lipofectamine PLUS transfection method. The day before transfection, HEK293 cells were seeded in two T75 flasks at a density of $2\times10^6$ cells/T75 flask in cell culturing medium without antibiotics. On the day of transfection, cells were washed with 1×DPBS and medium was replaced with Optimem to a volume of 5 mL/T75 flask before addition of Lipofectamine-plasmid complexes were added gently and drop wise to the cells in T75 flasks and replaced with growth medium after 3 hours and again to growth medium supplemented with 500 μg/mL G418 after 24 hours. After 4 weeks in G418 selection, clones were picked and tested in a functional assay. One clone was selected for use in compound profiling.

GLP-2 Receptor Efficacy Assay

The cAMP AlphaScreen® assay from Perkin Elmer was used to quantitate the cAMP response to activation of the GLP2 receptor. Teduglutide was used as a reference compound for GLP2 receptor activation. Data from test compounds eliciting an increase in the intracellular level of cAMP were normalized relative to the positive (Teduglutide) and negative control (vehicle) to calculate the EC50 and maximal response from the concentration response curve. The results are listed in Table 2.

TABLE 2

GLP-2R EC50 measurements

| ZP No. | EC50_Avg (nM) | EC50_SD (nM) |
|---|---|---|
| Teduglutide | 0.03 | 0.019 |
| ZP1848 | 0.3 | 0.14 |
| ZP2949 | 0.11 | 0.013 |
| ZP2711 | 0.072 | 0.0076 |
| ZP2469 | 0.052 | 0.0057 |
| ZP1846 | 0.26 | |

Example 3: Pharmacokinetic and Pharmacodynamic Profiling of GLP-2 Analogues

A phase 2 clinical trial was conducted to i.a. determine the PK profile of ZP1848 and metabolites in human SBS patients.

Method

The study was designed as a randomized, cross-over and double-blinded with three different doses of ZP1848 (10 mg, 1 mg, 0.1 mg) in 16 SBS patients.

The study protocol was approved by the Danish Medical Agency and The Danish Committee on Health Research Ethics.

The 18 SBS patients (16 patients completed the study) were randomized evenly and in a double-blinded fashion to each of the six cross-over dose level combinations: 10 mg/1 mg, 10 mg/0.1 mg, 1 mg/10 mg, 1 mg/0.1 mg, 0.1 mg/10 mg, 0.1 mg/1 mg of ZP1848. The patients were injected once daily (QD) subcutaneously with the above doses of ZP1848.

Blood samples for PK analysis were collected on several study visits throughout the study period: the study comprised a $1^{st}$ baseline balance study (4 days), a $1^{st}$ treatment period (21 days) including a $1^{st}$ treatment balance study (last 4 days of $1^{st}$ treatment period), followed by a wash-out period (at least 4 weeks); and a $2^{nd}$ baseline balance study (4 days), a $2^{nd}$ treatment period (21 days) including a $2^{nd}$ treatment balance study (last 4 days of $2^{nd}$ treatment period) and a follow-up period (at least 4 weeks).

PK sampling was performed at visit 11 (1st treatment, balance study) and visit 17 (second day of $2^{nd}$ baseline study—after a wash out period), and again at visit 25 ($2^{nd}$ treatment balance study) and at visit 29 (last day of follow-up period).

At day visit 11 and visit 25 a full PK profile in steady state was investigated. PK samples were taken prior to injection of ZP1848, and at the following time points (+/−10 minutes) after trial product administration: 1 h, 2 h, 4 h, 6 h, 8 h, 10 h, 12 h and 24 h. Each PK sample contained 2 mL of blood, resulting in a total of 46 mL blood drawn for PK purposes. The plasma sample was immediately stored at −80° C. after sampling.

Plasma samples were analyzed after immunoaffinity extraction followed by liquid chromatography mass spectrometry (LC-MS/MS). For each patient plasma concentrations were used for calculation of the pharmacokinetic parameters using the non-compartmental approach in Excel. Plasma terminal elimination half-life (T½) was determined as $\ln(2)/k_e$ where $k_e$ is the magnitude of the slope of the log linear regression of the log concentration versus time profile during the terminal phase.

Results

When ZP1848 is injected into the SC (subcutaneous) compartment, two functionally active metabolites are formed (ZP2469 and ZP2711, both C-terminal truncated analogs of glepaglutide, ZP1848). The overall PK profile of ZP1848 therefore comprises the effect of ZP1848 and its two main metabolites.

Both metabolites are pharmacologically active, as shown above, with in vitro potency comparable to ZP1848. The plasma level of ZP2711 is in the same range as that of ZP1848, whereas the plasma level of ZP2469 is multiple times higher than that of ZP1848. Consequently, it is necessary to include both metabolites when evaluating systemic exposure as they boths contribute to in vivo efficacy.

Due to the high plasma level of ZP2469 this compound has plasma level above the bioanalytical detection limit (50 pM for ZP2469, 25 pM for ZP1848 and ZP2711), hence it is possible to determined the half-life of compound ZP2469. A terminal plasma half-life of between 5 and 17 days, as shown in the table, suggests once weekly dosing of ZP1848 would be efficacious.

TABLE 3

PK results from Phase 2 clinical trial

| Subject | Compound | Day | Visit no | Conc. pM | Half-life (days) |
|---|---|---|---|---|---|
| 1003 | ZP2469 | 0 | 25 | 4490 | 7.2 |
| 1003 | ZP2469 | 32 | 29 | 209 | |
| 1007 | ZP2469 | 0 | 25 | 14700 | 7.2 |
| 1007 | ZP2469 | 36 | 29 | 460 | |
| 1008 | ZP2469 | 0 | 11 | 6770 | 9.5 |
| 1008 | ZP2469 | 56 | 17 | 116 | |
| 1010 | ZP2469 | 0 | 11 | 4340 | 11 |
| 1010 | ZP2469 | 56 | 17 | 112 | |
| 1013 | ZP2469 | 0 | 25 | 4940 | 9.6 |
| 1013 | ZP2469 | 35 | 29 | 394 | |
| 1014 | ZP2469 | 0 | 11 | 2220 | 5.2 |
| 1014 | ZP2469 | 28 | 17 | 52.8 | |
| 1015 | ZP2469 | 0 | 11 | 556 | 7.9 |
| 1015 | ZP2469 | 28 | 17 | 56.4 | |
| 1015 | ZP2469 | 0 | 25 | 3640 | 8.7 |
| 1015 | ZP2469 | 32 | 29 | 288 | |
| 1016 | ZP2469 | 0 | 11 | 4750 | 11 |

TABLE 3-continued

PK results from Phase 2 clinical trial

| Subject | Compound | Day | Visit no | Conc. pM | Half-life (days) |
|---|---|---|---|---|---|
| 1016 | ZP2469 | 49 | 17 | 236 | |
| 1018 | ZP2469 | 0 | 25 | 4660 | 8.7 |
| 1018 | ZP2469 | 40 | 29 | 195 | |
| 1020 | ZP2469 | 0 | 11 | 1040 | 12 |
| 1020 | ZP2469 | 35 | 17 | 133 | |
| 1013 | ZP2711 | 0 | 11 | 131 | 14 |
| 1013 | ZP2711 | 28 | 17 | 32.6 | |
| 1015 | ZP2711 | 0 | 25 | 543 | 10 |
| 1015 | ZP2711 | 32 | 29 | 61.4 | |

Example 4: Longitudinal Growth by Subcutaneous Administration of ZP1848 to Beagle Dogs for 39 Weeks Followed by a 6 Week Recovery Period Method ZP1848 (0.25, 1 or 5 mg/kg/day) was given for 39 weeks subcutaneously to beagle dogs (22 to 24 weeks). Vehicle was used as the control. Recovery from any effect was evaluated during a 6 week recovery period. The study was conducted in accordance with the applicable sections of the United Kingdom Animals (Scientific Procedures) Act 1986, Amendment Regulations 2012 (the Act).

After 39 weeks the dogs were sacrificed and all animals were subject to a detailed necropsy. The length of the small and large intestines were measured separately and recorded in centimeters. The entire length of the gastrointestinal tract (starting at the duodenum and ending at the rectum) was removed and trimmed of any excessive mesentery, connective or adipose tissue and the measurements for the small and large intestine recorded by laying the small intestine and large intestine on a clean surface and measured with a tape measure. The sections required for histopathology were left unopened and flushed through with water. The remainder were opened, cleaned with water, carefully blotted dry prior to weighing. On completion of length and weight measurements, the gastrointestinal tract was processed and fixed in 10% Neutral Buffered Formalin, as per standard necropsy practice for this species.

Results

There was an increase in small intestine length after 39 weeks of treatment at all doses and in both sexes, with the extent of the increase being greatest in males and females given 5 mg/kg/day where there was a 46% and 37% increase in males and females, respectively. This finding had partially recovered by the end of the six-week recovery period, with 16 and 19% increases from controls in males and females, respectively. In the same study, an increase in small intestine weight after 39 weeks of treatment at all doses and in both sexes, with the extent of the increase being greatest in males and females given 5 mg/kg/day where there was a 103% and 80% increase in males and females, respectively. This finding had partially recovered by the end of the six-week recovery period, with 78 and 34% increases from controls in males and females, respectively.

Example 5: A Phase 1, Open-Label, Partially Randomized, 3-Part, Parallel Group Trial to Evaluate the Pharmacokinetic Profile of Glepaglutide (ZP1848) after a Single Intravenous Injection and After Multiple Subcutaneous Injections in Healthy Human Subjects A Phase 1 clinical trial to characterize the pharmacokinetic (PK) profiles of glepaglutide (ZP1848) and its primary active metabolites following once-weekly and once daily subcutaneous (SC) injections and after a single intravenous (IV) infusion in healthy subjects was conducted. This included evaluating the pharmacodynamic effects on plasma citrulline levels following SC dosing in healthy subjects. The trial confirmed the feasibility of dosage regimes in which GLP-2 analogues are administered to patients in weekly dosage regimes and compare weekly dosage regimes with daily dosing.

Trial Design:

The trial design was a single-center, open-label, partially randomized, 3-part, parallel group trial to characterize the PK profile of glepaglutide administered by SC injection once daily for 7 days (Part 1), SC injection once weekly for 6 weeks (Part 2), and as a single IV infusion (Part 3) in healthy subjects.

In Part 1, eligible subjects were randomized 1:1 to Group A or B; in Part 2, eligible subjects were randomized 1:1 to Group C or D; all subjects in Part 3 (Group E) were assigned to the same dose level.

Number of Subjects:

Approximately 75 male and female subjects were enrolled, with 15 subjects in each of 5 dose groups, to ensure that at least 12 subjects complete each group.

Diagnosis and Main Criteria for Inclusion:

Healthy male and female subjects aged between 18 and 60 years, inclusive, with a body mass index (BMI) between 18.0 and 30.0 kg/m², inclusive, and preferably subjects have a BMI of ≤25.0 kg/m².

Test Products, Dose, and Mode of Administration:

Glepaglutide was supplied as an aqueous solution at concentrations of 2 and 10 mg/mL.

Group A: 1 mg glepaglutide once daily, given as single SC injections on Days 1 to 7.

Group B: 5 mg glepaglutide once daily, given as single SC injections on Days 1 to 7.

Group C: 5 mg glepaglutide once weekly, given as single SC injections on Days 1, 8, 15, 22, 29, and 36.

Group D: 10 mg glepaglutide once weekly, given as single SC injections on Days 1, 8, 15, 22, 29, and 36.

Group E: 1 mg glepaglutide, given as an IV infusion at a rate of 4 mg/h for 15 minutes on Day 1.

Duration of Treatment

Planned Screening duration: approximately 28 days

Total Duration (Screening to End of Trial):

Groups A and B: 71 days

Groups C and D: 100 days

Group E: 51 days

Criteria for Evaluation:

Pharmacokinetics:

Blood samples were collected for the analysis of plasma concentrations of glepaglutide and its primary active metabolites, ZP2469 (ZP1848$_{1-34}$) and ZP2711 (ZP1848$_{1-35}$); samples were assayed using validated analytical methods. The following PK parameter estimates were calculated using standard non-compartmental methods: terminal elimination half-life ($t_{1/2}$), total body clearance of drug after IV administration (CL; IV dose, parent drug only), apparent total clearance (CL/F; SC doses, parent drug only), volume of distribution at steady state ($V_{ss}$; IV dose, parent drug only), apparent volume of distribution at steady state ($V_{ss}/F$; SC doses, parent drug only), volume of distribution ($V_z$; IV dose, parent drug only), apparent volume of distribution ($V_z/F$; SC doses, parent drug only), maximum observed plasma concentration ($C_{max}$), area under the plasma concentration-time curve (AUC) over a dosing interval (AUC$_T$), AUC from time zero to infinity (AUC$_{inf}$), AUC from time zero to the time of the last measurable concentration (AUC$_{last}$), and time of the maximum observed plasma concentration (t$_{max}$). Metabolite exposure (based on C$_{max}$, AUC$_T$, and AUC$_{inf}$) were determined for each group as a ratio of the 2 primary active metabolites, ZP2469 (ZP1848$_{1-34}$) and ZP2711 (ZP1848$_{1-35}$), relative to the glepaglutide parent drug.

Pharmacodynamics:

Blood samples were collected for the measurement of plasma citrulline (for SC doses only).

Statistical Methods:

Pharmacokinetics:

The PK parameters estimates for glepaglutide, ZP2469 (ZP1848$_{1-34}$), and ZP2711 (ZP1848$_{1-35}$) were listed and summarized using standard descriptive statistics. The primary PK parameters are t$_{1/2}$ for glepaglutide, ZP2469 (ZP1848$_{1-34}$), and ZP2711 (ZP1848$_{1-35}$); and CL (IV dose), CL/F (SC doses), V$_{ss}$ (IV dose), V$_{ss}$/F (SC dose), V$_z$ (IV dose), and V$_z$/F (SC doses) for glepaglutide. The half-life is calculated as LN(2)/k$_e$ where ÷k$_e$ is estimate from the slope of the terminal part of the LN(concentration) versus time curve, with repeats regressions of LN(concentration) values using the last three points with non-zero concentrations, then the last four points, last five points, etc. Points with a concentration value of zero are not included. Points prior to C$_{max}$ are not used. For each regression, an Adjusted-R$^2$ is computed: Adjusted-R$^2$=1−((1−R$^2$)×(n−1))/(n−2); where n is the number of data points in the regression and R$^2$ is the square of the correlation coefficient. k$_e$ using the regression with the largest adjusted R$^2$ and, 1) If the adjusted R$^2$ does not improve, but is within 0.0001 of the largest adjusted R$^2$ value, the regression with the larger number of points is used. 2) k$_e$ must be calculated from at least three data points. 3) The estimated slope must be negative, so that its negative k$_e$ is positive. The results of the calculations carried out with preliminary data are shown in Table 4, while the results of the calculations with the complete final data set are shown in Table 5.

Pharmacodynamics:

Plasma citrulline concentrations and changes from baseline were listed and summarized using descriptive statistics.

Results:

Initial results and analysis for a selection of subjects enrolled in Groups A, B, C and D found that ZP2469 had a half-life in hours as shown in the Table 4 below. The half-life found using once weekly dosing supports the feasibility of using dosing of the GLP-2 peptides of the present invention once weekly or twice weekly.

TABLE 4

Half-life preliminary results

| | | No Doses | | |
| --- | --- | --- | --- | --- |
| | | 1 | 6 | 7 |
| | Subject | | Half-life | |
| Group | No. | | ZP2469 (hr) | |
| A | 101 | | | 20 |
| Once Daily | 104 | | | 95 |
| | 105 | | | 76 |
| | 109 | | | 36 |
| | 110 | | | 33 |
| | 112 | | | 87 |
| B | 102 | | | 94 |
| Once Daily | 103 | | | 75 |
| | 106 | | | 108 |
| | 107 | | | 209 |

TABLE 4-continued

Half-life preliminary results

| | | No Doses | | |
| --- | --- | --- | --- | --- |
| | | 1 | 6 | 7 |
| | Subject | | Half-life | |
| Group | No. | | ZP2469 (hr) | |
| | 108 | | | 59 |
| | 111 | | | 139 |
| C | 201 | 38 | 11 | |
| Once weekly | 203 | 100 | 17 | |
| | 204 | 17 | 16 | |
| | 208 | 38 | 32 | |
| | 209 | 48 | 40 | |
| | 212 | 20 | 22 | |
| D | 202 | 56 | 60 | |
| Once weekly | 205 | 52 | 55 | |
| | 206 | 38 | 74 | |
| | 207 | 43 | 34 | |
| | 211 | 34 | 58 | |

Once the study was completed, a final more complete data set became available and was also used to calculate the half-life. The half-life calculated in the specific time period from 72 to 168 hours after dosing (regardless of the Adjusted-R$^2$~value and number data points) for the metabolite ZP2469 is shown in the Table 5 below.

TABLE 5

Half-life final results

| | | Number of doses | | |
| --- | --- | --- | --- | --- |
| | | 1 | 6 | 7 |
| | | | Half-life of ZP2469 in | |
| | | | the interval from 72 to | |
| Group | Subject | | 168 hours post dose (hr) | |
| A | 105 | | | 75 |
| 1 mg | 112 | | | 87 |
| once daily | 115 | | | 94 |
| | 119 | | | 80 |
| | 125 | | | 54 |
| | 126 | | | 57 |
| B | 102 | | | 42 |
| 5 mg | 103 | | | 168 |
| once daily | 106 | | | 77 |
| | 107 | | | 101 |
| | 108 | | | 53 |
| | 111 | | | 101 |
| | 114 | | | 34 |
| | 116 | | | 46 |
| | 122 | | | 100 |
| | 123 | | | 94 |
| | 127 | | | 40 |
| | 128 | | | 84 |
| | 129 | | | 50 |
| C | 203 | 329 | 26 | |
| 5 mg | 204 | 41 | 35 | |
| once weekly | 208 | 38 | 59 | |
| | 209 | 48 | 94 | |
| | 212 | 59 | 75 | |
| | 213 | 48 | 57 | |
| | 214 | 61 | 43 | |
| | 216 | NA | 52 | |
| | 219 | 217 | 107 | |
| | 221 | 45 | 33 | |
| | 222 | 39 | 68 | |
| | 225 | NA | 47 | |
| | 226 | 91 | 65 | |
| | 229 | 75 | 452 | |

TABLE 5-continued

Half-life final results

| | | Number of doses | |
|---|---|---|---|
| | | 1 | 6 7 |
| | | Half-life of ZP2469 in the interval from 72 to | |
| Group | Subject | 168 hours post dose (hr) | |
| D | 202 | 66 | 60 |
| 10 mg | 205 | 54 | 55 |
| once weekly | 206 | 120 | 74 |
| | 207 | 36 | 58 |
| | 210 | 46 | NA |
| | 211 | 35 | 70 |
| | 215 | 60 | 59 |
| | 217 | 26 | 30 |
| | 218 | 158 | 102 |
| | 220 | 53 | 53 |
| | 223 | 43 | 60 |
| | 224 | 33 | 42 |
| | 227 | 45 | 48 |
| | 228 | 43 | 56 |
| | 230 | 38 | 17 |

Example 6: Intestinotrophic Effects of Glepaglutide Following Chronic Exposure in Rats Methods:

Wistar rats were dosed subcutaneously (SC) with vehicle, 1, 3 and 10 mg/kg ZP1848 on a daily basis for 26 weeks. Further sub-groups of control and high-dose animals were allowed a 6-week recovery period following completion of the dosing period. Sub-groups of control and high-dose animals were allowed a 6-week recovery period following completion of the dosing period. The length and the weight of the small and large intestines were measured at necropsy as indicators of intestinotrophic effects and the intestinal tract was evaluated histologically.

Results:

ZP1848 induced dose-related significant ($p<0.01$) increases in length and weight of the small intestines in rats (see Table 5). Furthermore, the length and weight of the large intestine was also slightly increased. ZP1848 produced a dose-related increase in mucosal hyperplasia of the duodenum, jejunum and ileum. Interestingly, at the end of the recovery period significant intestinotrophic effects were still present in the high-dose groups although partial recovery was seen.

TABLE 6

Percentage (%) increase relative to control group (males/females)

| | Main Study animals | Recovery animals |
|---|---|---|
| Dose (mg/kg) | 10 | 10 |
| SI length | 38/47 | 39/45 |
| SI weight | 190/238 | 85/101 |

SI = small intestine

Conclusion:

A significant dose-related intestinotrophic effect was seen following 26 weeks of ZP1848 exposure in rats. A similar effect was also seen after 7 days of dosing in rats. At all doses in the 26 week study, increased length and weight, as well as macroscopic thickening and villous hypertrophy, were noted in all segments of the small intestine. These findings were still present following a 6-week recovery period, indicating prolonged intestinotrophic effects of glepaglutide.

Example 7: Absolute Changes in Absolute Fecal Wet Weight Output in SBS-IF/SBS-II Patients Method The study was designed as a randomized, cross-over and double-blinded with three different doses of ZP1848 (10 mg, 1 mg, 0.1 mg) in 16 SBS patients. The study protocol was approved by the Danish Medical Agency and The Danish Committee on Health Research Ethics.

The 18 SBS patients were randomized evenly and in a double-blinded fashion to each of the six cross-over dose level combinations: 10 mg/1 mg, 10 mg/0.1 mg, 1 mg/10 mg, 1 mg/0.1 mg, 0.1 mg/10 mg, 0.1 mg/1 mg of ZP1848. The SBS patient group comprised 9 females, 9 males; hereof 13 SBS-IF patients and 5 SBS-II patients. Mean age was 62 years, mean short bowel length was 110 cm, and two SBS-IF patients had >50% colon in continuity. The patients were injected once daily subcutaneously with the above doses of ZP1848.

The aim of this study was to evaluate efficacy of ZP1848 on fecal wet weight output in patients with SBS-II and SBS-IF and thus the absolute change from baseline in wet weight of fecal output as measured by metabolic balance studies prior to and on the last 3 days of each treatment period.

Results:

Of the 18 patients randomized and treated with ZP1848, 16 completed the trial. The results changes in absolute fecal wet weight output (g/day) are shown in the below Table 7. The improvements were of the same magnitude in all patient groups, i.e. SBS-II, SBS-IF and patients with colon in continuity. This demonstrates that ZP1848 is effective for the treatment of both classes of SBS patients. Furthermore, the present inventors believe that these results support that GLP-2 analogues therapy using ZP1848 is effective in preventing or treating SBS-II patients becoming SBS-IF.

TABLE 7

Changes in absolute fecal wet weight output, SBS-II vs SBS-IF

| Changes in Absolute Fecal Wet Weight Output (g/day) (Means [95% CI]) | 0.1 mg | 1 mg | 10 mg | 1 mg + 10 mg |
|---|---|---|---|---|
| II + IF (n = 16) | 173 [−160, 506] p = 0.274 | −592 [−913, −272] p = 0.002 | −833 [−1152, −515] p = 0.0002 | −713 [−935, −490] p < 0.0001 |
| IF (n = 11) | 196 [−301, 693] p = 0.3575 | −587 [−1080, −95] p = 0.0280 | −894 [−1420, −368] p = 0.0072 | −741 [−1079, −402] p = 0.0025 |
| II (n = 5) | −37 [−873, 800] p = 0.9094 | −303 [−1310, 704] p = 0.4503 | −837 [−1495, −178] p = 0.0243 | −570 [−1459, −45] p = 0.0393 |

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The invention claimed is:

1. A method of for increasing absorptive capacity of a small intestine by elongating, macroscopic thickening, and villous hypertrophy of the small intestine in a subject in need thereof with reduced small intestine absorptive capacity, the method comprising administering by subcutaneous injection once or twice weekly a pharmaceutical composition comprising from 10 to 30 mg/mL of a GLP-2 analogue represented by the formula:

H-HGEGTFSSELATILDALAARDFIAWLIAT-KITDKKKKKK-NH2 (1848) (SEQ ID NO: 2), or a pharmaceutically acceptable salt thereof, wherein the subcutaneous injection forms a subcutaneous depot that slowly releases the GLP-2 analogue resulting in a terminal plasma half-life that is longer in comparison to when the pharmaceutical composition is administered intravenously, allowing once or twice weekly subcutaneous administration as opposed to daily intravenous administration.

2. The method of claim 1, wherein the subcutaneous depot comprises between 1 and 20 mg of the GLP-2 analogue.

3. The method of claim 2, wherein the subcutaneous depot comprises between 1 and 10 mg of the GLP-2 analogue.

4. The method of claim 3, wherein the subcutaneous depot comprises between 2 and 7 mg of the GLP-2 analogue.

5. The method of claim 1, wherein the subcutaneous depot comprises 10 mg of the GLP-2 analogue.

6. The method of claim 1, wherein the subject in need thereof is suffering from a stomach or bowel-related disorder.

7. The method of claim 6, wherein the method comprises subcutaneously injecting once weekly 10 mg of a GLP-2 analogue into the subject.

8. The method of claim 6, wherein the method comprises subcutaneously injecting twice weekly 10 mg of a GLP-2 analogue into the subject.

9. The method of claim 6, wherein the subject in need thereof is suffering from short bowel syndrome.

* * * * *

```
                         SEQUENCE LISTING

Sequence total quantity: 11
SEQ ID NO: 1            moltype = AA  length = 33
FEATURE                 Location/Qualifiers
source                  1..33
                        mol_type = protein
                        organism = Homo sapiens
SEQUENCE: 1
HADGSFSDEM NTILDNLAAR DFINWLIQTK ITD                                33

SEQ ID NO: 2            moltype = AA  length = 39
FEATURE                 Location/Qualifiers
source                  1..39
                        mol_type = protein
                        note = Synthetic peptide sequence
                        organism = synthetic construct
SEQUENCE: 2
HGEGTFSSEL ATILDALAAR DFIAWLIATK ITDKKKKKK                          39

SEQ ID NO: 3            moltype = AA  length = 36
FEATURE                 Location/Qualifiers
source                  1..36
                        mol_type = protein
                        note = Synthetic peptide sequence
                        organism = synthetic construct
SEQUENCE: 3
HGEGTFSSEL ATILDALAAR DFIAWLIATK ITDKKK                             36

SEQ ID NO: 4            moltype = AA  length = 35
FEATURE                 Location/Qualifiers
source                  1..35
                        mol_type = protein
                        note = Synthetic peptide sequence
                        organism = synthetic construct
SEQUENCE: 4
HGEGTFSSEL ATILDALAAR DFIAWLIATK ITDKK                              35

SEQ ID NO: 5            moltype = AA  length = 34
FEATURE                 Location/Qualifiers
source                  1..34
                        mol_type = protein
                        note = Synthetic peptide sequence
                        organism = synthetic construct
SEQUENCE: 5
HGEGTFSSEL ATILDALAAR DFIAWLIATK ITDK                               34

SEQ ID NO: 6            moltype = AA  length = 33
FEATURE                 Location/Qualifiers
source                  1..33
                        mol_type = protein
                        note = Synthetic peptide sequence
                        organism = synthetic construct
SEQUENCE: 6
HGEGTFSSEL ATILDALAAR DFIAWLIATK ITD                                33

SEQ ID NO: 7            moltype = AA  length = 33
FEATURE                 Location/Qualifiers
source                  1..33
                        mol_type = protein
                        note = Synthetic peptide sequence
                        organism = synthetic construct
SEQUENCE: 7
HGEGTFSSEL ATILDALAAR DFIAWLIATK ITD                                33

SEQ ID NO: 8            moltype = AA  length = 39
FEATURE                 Location/Qualifiers
source                  1..39
                        mol_type = protein
                        note = Synthetic peptide sequence
                        organism = synthetic construct
SEQUENCE: 8
HGEGSFSSEL STILDALAAR DFIAWLIATK ITDKKKKKK                          39
```

```
SEQ ID NO: 9            moltype = AA  length = 33
FEATURE                 Location/Qualifiers
source                  1..33
                        mol_type = protein
                        note = Synthetic peptide sequence
                        organism = synthetic construct
SEQUENCE: 9
HGEGSFSSEL STILDALAAR DFIAWLIATK ITD                              33

SEQ ID NO: 10           moltype = AA  length = 34
FEATURE                 Location/Qualifiers
source                  1..34
                        mol_type = protein
                        note = Synthetic peptide sequence
                        organism = synthetic construct
SEQUENCE: 10
HGEGSFSSEL STILDALAAR DFIAWLIATK ITDK                             34

SEQ ID NO: 11           moltype = AA  length = 35
FEATURE                 Location/Qualifiers
VARIANT                 1
                        note = misc_feature - Xaa is absent or a peptide sequence
                         of 1-6 amino acid units of Lys (e.g., K, KK, KKK, KKKKK,
                         KKKKK, KKKKKK)
VARIANT                 6
                        note = misc_feature - Xaa is Ser or Thr
VARIANT                 12
                        note = misc_feature - Xaa is Ala or Ser
VARIANT                 35
                        note = misc_feature - Xaa is absent or a peptide sequence
                         of 1-6 amino acid units of Lys (e.g., K, KK, KKK, KKKKK,
                         KKKKK, KKKKKK)
source                  1..35
                        mol_type = protein
                        organism = synthetic construct
SEQUENCE: 11
XHGEGXFSSE LXTILDALAA RDFIAWLIAT KITDX                            35
```